US012788317B2

(12) United States Patent
Karsikas et al.

(10) Patent No.: US 12,788,317 B2
(45) Date of Patent: Nov. 10, 2026

(54) TECHNIQUES FOR DETERMINING A CIRCADIAN RHYTHM CHRONOTYPE

(71) Applicant: Oura Health Oy, Oulu (FI)

(72) Inventors: Mari Pauliina Karsikas, Oulu (FI); Henri Matti Johannes Huttunen, Yli-Siurua (FI); Iman Alikhani, Espoo (FI)

(73) Assignee: Oura Health Oy, Oulu (FI)

( * ) Notice: Subject to any disclaimer, the term of this patent is extended or adjusted under 35 U.S.C. 154(b) by 478 days.

(21) Appl. No.: 18/320,943

(22) Filed: May 19, 2023

(65) Prior Publication Data

US 2023/0371890 A1 Nov. 23, 2023

Related U.S. Application Data

(60) Provisional application No. 63/344,800, filed on May 23, 2022.

(51) Int. Cl.

*A61B 5/00* (2006.01)
*A61B 5/0205* (2006.01)
*A61B 5/11* (2006.01)

(52) U.S. Cl.

CPC .......... *A61B 5/4857* (2013.01); *A61B 5/0205* (2013.01); *A61B 5/1118* (2013.01);
(Continued)

(58) Field of Classification Search

CPC ... A61B 5/4857; A61B 5/0205; A61B 5/1118; A61B 5/4806; A61B 5/486;
(Continued)

(56) References Cited

U.S. PATENT DOCUMENTS 10,076,286 B1 9/2018 Bajaj et al.
2017/0132946 A1* 5/2017 Kinnunen .............. A61B 5/165
(Continued)

FOREIGN PATENT DOCUMENTS

CN 101320523 A 12/2008
JP 2022-515374 A 2/2022

OTHER PUBLICATIONS

International Search Report and Written Opinion—PCT/US2023/067301—ISA/EPO—May 22, 2023.
(Continued)

*Primary Examiner* — Amanda L Steinberg
(74) *Attorney, Agent, or Firm* — ArentFox Schiff LLP

(57) ABSTRACT

Methods, systems, and devices for determining a circadian rhythm chronotype are described. A system may be configured to receive a first set of physiological data collected over a period of time and receive a second set of physiological data collected over a previous sleep day. Additionally, the system may be configured to classify, using a machine learning model, the first set of physiological data into the circadian rhythm chronotype. The system may then compare the determined circadian rhythm chronotype and the received second set of physiological data. The system may cause a graphical user interface of the user device to display a message associated with the comparison, the determined circadian rhythm chronotype, the received second set of physiological data, or a combination thereof.

20 Claims, 13 Drawing Sheets

(52) U.S. Cl.
CPC ............ *A61B 5/4806* (2013.01); *A61B 5/486* (2013.01); *A61B 5/6826* (2013.01); *A61B 5/7267* (2013.01); *A61B 5/742* (2013.01); *A61B 2560/0252* (2013.01)

(58) Field of Classification Search
CPC ..... A61B 5/6826; A61B 5/7267; A61B 5/742; A61B 2560/0252
See application file for complete search history.

(56) References Cited

U.S. PATENT DOCUMENTS

| | | | | |
|---|---|---|---|---|
| 2017/0231562 | A1* | 8/2017 | Park | A61B 5/7235 600/485 |
| 2018/0289314 | A1* | 10/2018 | Reifman | A61B 5/165 |
| 2021/0186419 | A1 | 6/2021 | Van Ee et al. | |
| 2021/0241649 | A1 | 8/2021 | Kinnunen et al. | |
| 2021/0401377 | A1 | 12/2021 | Pho et al. | |
| 2022/0105308 | A1* | 4/2022 | Youngblood | G16H 15/00 |
| 2024/0000375 | A1 | 1/2024 | Shaw et al. | |

OTHER PUBLICATIONS

Office Action received for Japanese Patent Application No. 2024-569392, mailed on Jan. 27, 2026, 11 pages (6 pages of English Translation, 5 pages of Original Document).
Third Party Observation received for Indian Patent Application No. 202417091143, mailed on May 20, 2025, 67 pages.
Hannay et al., "Integrating wearable data into circadian models", Curr Opin Syst Biol., vol. 22, Aug. 2020, pp. 1-12.
Office Action received for Australian Patent Application No. 2023275705, mailed on Sep. 17, 2026, 7 pages.

* cited by examiner

TECHNIQUES FOR DETERMINING A CIRCADIAN RHYTHM CHRONOTYPE

CROSS REFERENCE

The present Application for Patent claims the benefit of U.S. Provisional Patent Application No. 63/344,800 by KARSIKAS et al., entitled "TECHNIQUES FOR DETERMINIG A CIRCADIAN RHYTHM CHRONOTYPE," filed May 23, 2022, assigned to the assignee thereof, and expressly incorporated by reference herein.

FIELD OF TECHNOLOGY

The following relates to wearable devices and data processing, including techniques for determining a circadian rhythm chronotype.

BACKGROUND

Some wearable devices may be configured to collect data from users associated with body temperature and heart rate. For example, some wearable devices may be configured to determine a user's chronotype associated with one or more physiological parameters or characteristics. However, conventional chronotype techniques implemented by wearable devices may be limited in their utility, because they may only take into account a limited number of inputs or variables, resulting in inaccurate chronotype classification.

DETAILED DESCRIPTION

Figure 1:
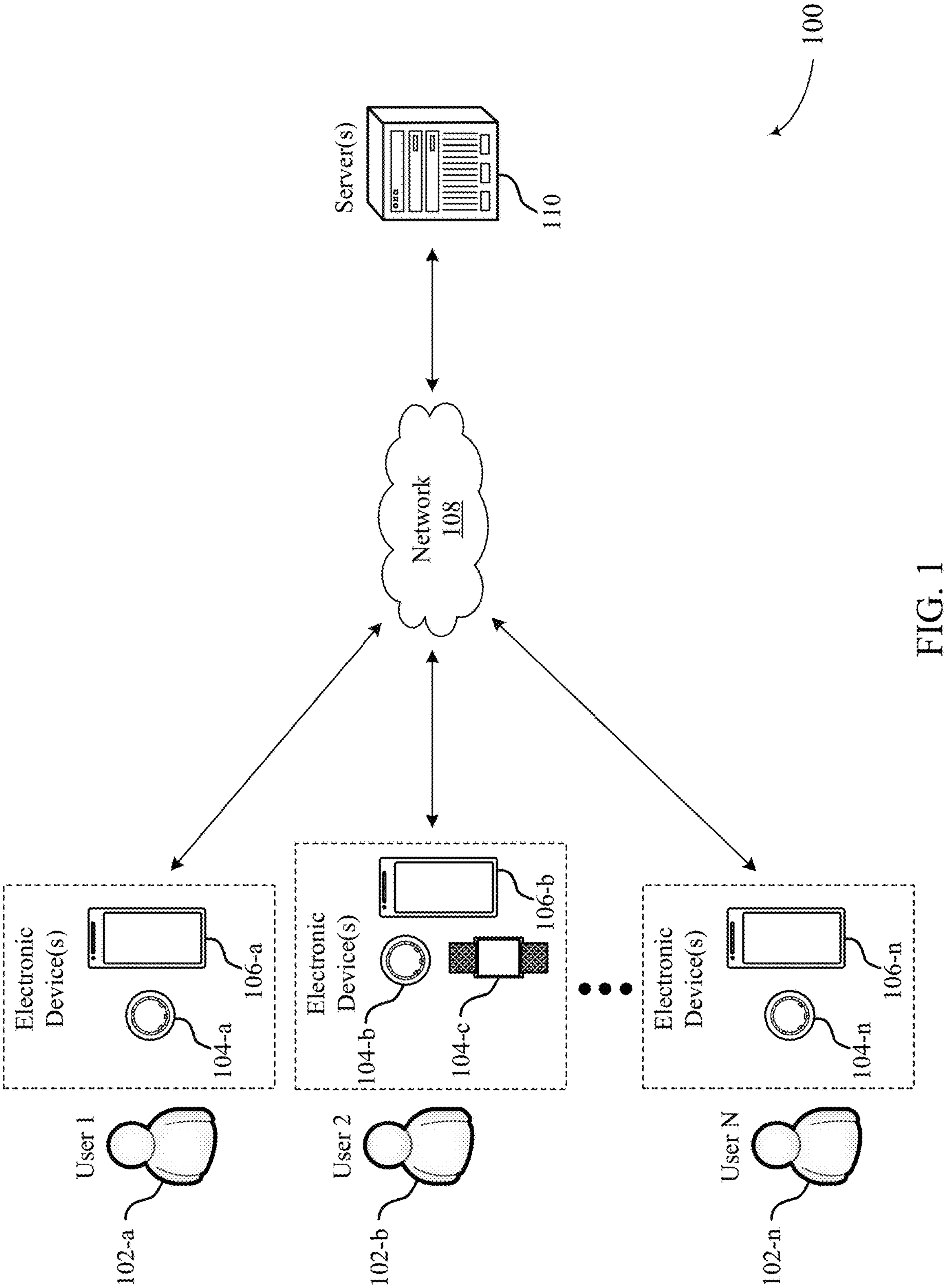
FIG. 1 illustrates an example of a system that supports techniques for determining a circadian rhythm chronotype in accordance with aspects of the present disclosure.

Some wearable devices may be configured to collect physiological data from users, including temperature data, heart rate data, heart rate variability (HRV) data, sleep data, respiratory data, and the like. Acquired physiological data may be used to analyze behavioral and physiological characteristics associated with the user, such as movement, sleep patterns, activity patterns, and the like. Many users have a desire for more insight regarding their physical health, including their sleeping patterns, activity, and overall physical well-being. In particular, many users may have a desire for more insight regarding their circadian rhythm, chronotypes, and misalignments with their circadian rhythm. However, typical tracking or health devices and applications lack the ability to provide robust determination and insight for several reasons.

First, procedures for determining and understanding chronotypes may rely on self-report scales or questionnaires, that introduce a number of biases into the calculation. The questionnaires may consist of a set of questions about the preference of the individual for sleep, activity time onset, activity time offset, regularity of sleep, and the like. However, self-report assessments may be subjective. Second, even for devices that are wearable or that measure a user's biomarkers, typical devices and applications lack the ability to collect other physiological, behavioral, or contextual inputs from the user that can be combined with the measured physiological parameters such as temperature data, sleep data, and the like to more comprehensively understand the complete set of physiological contributors to a user's circadian rhythm and associated chronotype.

Aspects of the present disclosure are directed to techniques for determining a circadian rhythm chronotype. In particular, computing devices of the present disclosure may receive physiological data from a wearable device associated with the user and collected over a period of time. The physiological data may include at least nighttime temperature data, activity data, sleep pattern data, or some combination or subset of these measurements. Aspects of the present disclosure may classify, using a machine learning model, the physiological data from the wearable device into a circadian rhythm chronotype based on the nighttime temperature data, the activity data, the sleep pattern data, or a combination thereof. As described in more detail below, the circadian rhythm chronotype classification may additionally or alternatively involve different physiological inputs and/or different chronotype classifications as inputs.

For the purposes of the present disclosure, the term "circadian rhythm chronotype," "circadian chronotype," "or "circadian profile," and like terms, may be used to refer to an individual circadian rhythmicity, that is related to sleep, diet, physical activity patterns, and the like. The circadian rhythm is a biological, internal process running in the background of daily functions and orchestrating a twenty-four hour cycle (or an approximately twenty-four hour cycle) in the users. The circadian rhythm regulates biological functions and processes, including but not limited to sleep-wake cycle, alertness, digestion, body temperature, hormone release, and the like. In some cases, a user's circadian rhythm (e.g., body clock) may be externally sensitive and influenced by lifestyle choices and other factors. For example, exposure to the light at different times of the day, crossing multiple time zones, and working in variable shifts may be examples that influence the internal body clock.

In some cases, the determined circadian rhythm chronotype may be compared with received physiological data from a previous calendar day (e.g., including a previous night's sleep for a night proceeding the current calendar day). For example, the determined circadian rhythm chronotype may be compared with sleep data from last night's sleep. In such cases, the system may determine whether a user's most recent sleep data is aligned with the user's determined circadian rhythm chronotype. During a circadian rhythm misalignment, the body systems cease to function optimally and many users may suffer from significant sleep disruption due to a circadian rhythm misalignment, for example, as well as decreases in alertness, academic performance, athletic performance, and other symptoms that decrease quality of life and also mark an increased risk for insomnia and chronic health conditions (e.g., sleep disturbances, irritability, anxiety, obesity, diabetes, depression, and seasonal affective disorder).

In some cases, determining the circadian rhythm chronotype and detecting misalignment at an early stage may reduce later-life health risks, specifically risks for cardiovascular disease and cognitive dysfunction. In such cases, techniques to determine the circadian rhythm chronotype, in order to improve quality of life, sleep, and mood, and to reduce future health risks, may be desired. For example, methods and techniques to help users understand in a personalized way their circadian rhythm chronotype and how to optimize lifestyle changes to reduce misalignment may be desired.

Some aspects of the present disclosure are directed to the measuring and/or receiving of physiological data or signals that are regulated and influenced by the circadian rhythm. For example, the signals may include, but are not limited to, sleep-wake cycle, physical activity, temperature, heart rate, restorative time, and the like. In some implementations, a computing device may be able to cause a graphical user interface (GUI) of a user device to display a graphical representation of an averaging over a period of time of one or more measured or calculated physiological parameters or characteristics such as sleep pattern data. For example, the graphical representation may include the averaging over the period of time of the one or more measured or calculated physiological parameters and a second set of physiological data including at least sleep data from the previous night's sleep.

In such cases, the computing devices may generate a behavioral and physiological picture of a user's twenty-four hour clock from their physiological data. For example, the system may create a prototype report from circadian rhythm related data that may include wake time and bedtime (e.g., sleep duration), sleep regularity of the user in the timeframe that the report is processed from, distribution of physical activity (e.g., metabolic equivalent of task (MET)) data that may demonstrate the user's energy expenditure at different times of the day, overall sleep temperature variation of the user, or a combination thereof.

Techniques described herein may notify a user of their determined circadian rhythm chronotype in a variety of ways, including the graphical representation of the averaging over the period of time. For example, a system may cause the GUI of a user device to display a message or other notification to notify the user of the determined circadian rhythm chronotype, and make recommendations to the user. In one example, the GUI may display a recommended time of day that the user is active, a recommended wake time that the user wakes up, a recommended bedtime that the user goes to sleep, a recommended sleep duration, a recommended time of day that the user rests, or a combination thereof. A GUI may also include graphics/text that indicate a misalignment between the received additional physiological data and the determined circadian rhythm chronotype. In such cases, the message or notification may be generated based on the misalignment.

In some cases, understanding the user's circadian rhythm chronotype may allow the user to schedule sleep and daily activities such that the body may function on the user's own personalized circadian rhythm. For example, determining and understanding the circadian rhythm chronotype may enable the user to enhance mental, emotional, and physical performance considering that an alertness timeline is different among morning and evening type individuals throughout the day as well as recommending a bedtime and wake time that suits the user's determined chronotype, thereby improving the overall health of the user.

Aspects of the disclosure are initially described in the context of systems supporting physiological data collection from users via wearable devices. Additional aspects of the disclosure are described in the context of example timing diagrams and example GUIs. Aspects of the disclosure are further illustrated by and described with reference to apparatus diagrams, system diagrams, and flowcharts that relate to techniques for determining a circadian rhythm chronotype.

FIG. 1 illustrates an example of a system 100 that supports techniques for determining a circadian rhythm chronotype in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, blood oxygen saturation (SpO2), blood sugar levels (e.g., glucose metrics), and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as light emitting diodes (LEDs) (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs) (e.g., vertical cavity surface-emitting lasers (VCSELs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data. In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks," 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for determining a circadian rhythm chronotype based on data collected by a wearable device 104. In particular, the system 100 illustrated in FIG. 1 may support techniques for determining the circadian rhythm chronotype of a user 102 and causing a user device 106 corresponding to the user 102 to display a graphical representation of an averaging over a period of time (e.g., the last 30 or 60 days) of sleep pattern data relative to sleep pattern data from a previous night's sleep.

For example, as shown in FIG. 1, User 1 (user 102-*a*) may be associated with a wearable device 104-*a* (e.g., ring 104-*a*) and a user device 106-*a*. In this example, the ring 104-*a* may collect data associated with the user 102-*a*, including continuous nighttime temperature data, activity data, sleep pattern data, heart rate, and the like. As used herein, "continuous" nighttime temperature may refer to the ability of the system 100 to sample the user's 102-*a* temperature continuously throughout the day and/or night at a sufficient rate (e.g., one sample per minute) to provide sufficient temperature data for analysis described herein.

In some aspects, data collected by the ring 104-*a* may be used to classify, using a machine learning model, the physiological data from the wearable device 104-*a* into a circadian rhythm chronotype for User 1. Determining the circadian rhythm chronotype may be performed by any of the components of the system 100, including the ring 104-*a*, the user device 106-*a* associated with User 1, the one or more servers 110, or any combination thereof. Upon determining the circadian rhythm chronotype, the system 100 may selectively cause the GUI of the user device 106-*a* to display a graphical representation indicative of the determined chronotype, the one or more physiological parameters used to classify the chronotype, or some combination of this information.

For example, the system 100 may cause the GUI of the user device 106-*a* to display an averaging over a period of time of at least the sleep pattern data. In other examples, the system 100 may cause the GUI of the user device 106-*a* to display sleep pattern data of User 1 from a previous night's sleep. In some examples, this information may be displayed simultaneously in a way that allows a user to easily see multiple types of information overlaid onto a time scale (e.g., a 24-hour clock face or the like) so that multiple insights or relationships among the different physiological parameters or chronotype may become apparent (e.g., average go-to-bed or wake-up times compared to last night's go-to-bed or wake-up times).

In some implementations, upon receiving physiological data (e.g., including at least continuous nighttime temperature data, activity data, and sleep pattern data), the system 100 may classify the physiological data into the circadian rhythm chronotype (e.g., determine whether you are an active person, have a regular sleep schedule, etc.) using the machine learning model. In some examples, the system 100 may overlay the graphical representation of the averaging over the period of time of at least the sleep pattern data and the sleep pattern data from the previous night's sleep against a circular representation of a twenty-four hour timespan. In such cases, the system 100 may cause the GUI of the user device 106-*a* to display a first segment that includes the averaging of the sleep pattern data over the period of time and a second segment that includes the sleep pattern data from the previous night's sleep.

In some cases, the system 100 may display to User 1 (e.g., via a GUI of the user device 106) the first segment and the second segment. In some implementations, the system 100 may generate alerts, messages, or recommendations for User 1 (e.g., via the ring 104-*a*, user device 106-*a*, or both) based on the determined circadian rhythm chronotype, where the alerts may provide insights regarding a misalignment between received physiological data and the determined circadian rhythm chronotype. In some cases, the messages may provide insights regarding a recommended time of day to exercise, wake up, go to sleep, rest, or a combination thereof.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
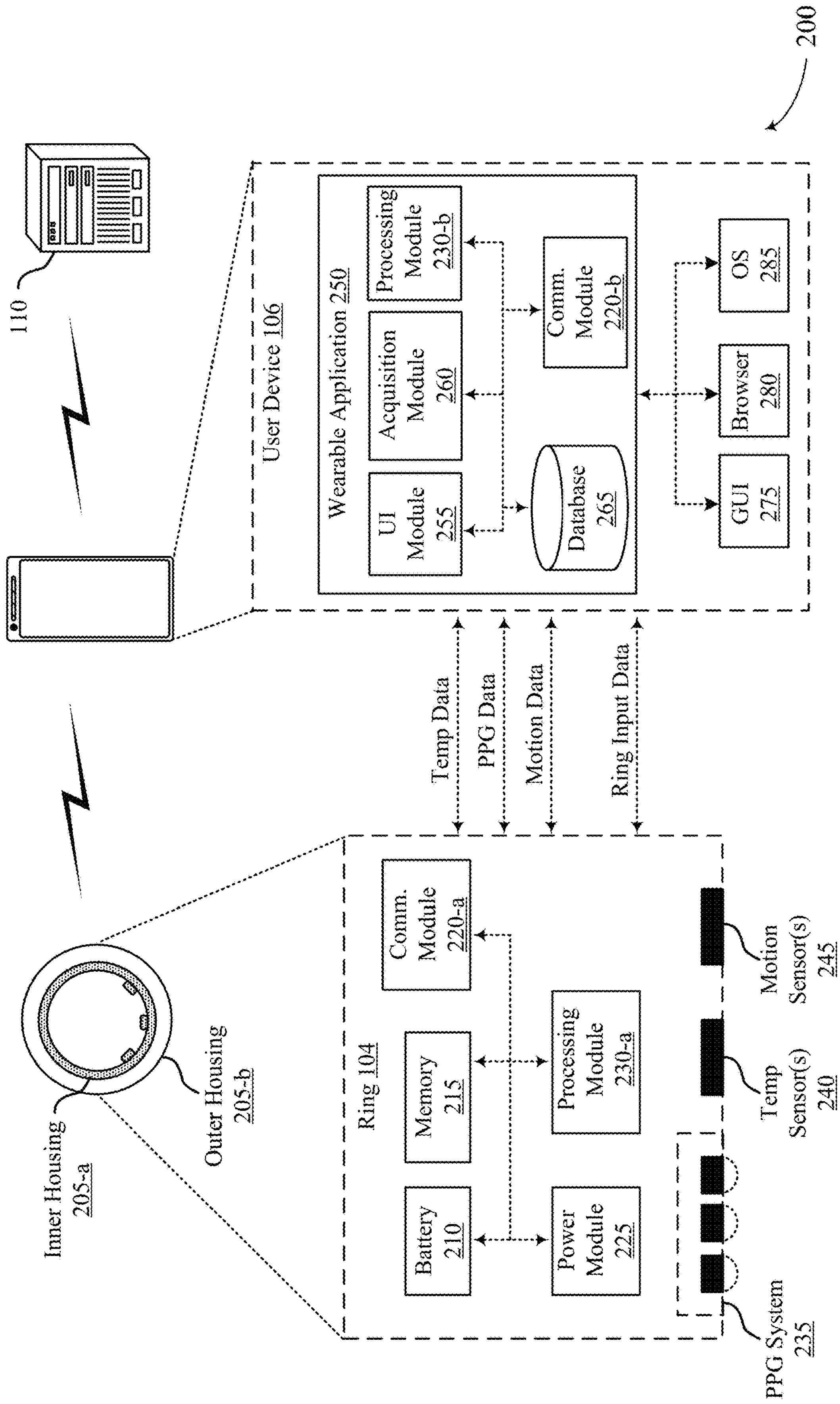
FIG. 2 illustrates an example of a system that supports techniques for determining a circadian rhythm chronotype in accordance with aspects of the present disclosure.

FIG. 2 illustrates an example of a system 200 that supports techniques for determining a circadian rhythm chronotype in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels (SpO2), blood sugar levels (e.g., glucose metrics), and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using adhesives, wraps, clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG LEDs. In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during charging, and under voltage during discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, that may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BMI 160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., “app”) that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given “sleep day.” In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, “sleep days” may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a “cut-off time,” where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more “contributors,” “factors,” or “contributing factors.” For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The “total sleep” contributor may refer to the sum of all sleep periods of the sleep day. The “efficiency” contributor may reflect the percentage of time spent asleep compared to time spent awake while in bed, and may be calculated using the efficiency average of long sleep periods (e.g., primary sleep period) of the sleep day, weighted by a duration of each sleep period. The “restfulness” contributor may indicate how restful the user's sleep is, and may be calculated using the average of all sleep periods of the sleep day, weighted by a duration of each period. The restfulness contributor may be based on a “wake up count” (e.g., sum of all the wake-ups (when user wakes up) detected during different sleep periods), excessive movement, and a “got up count” (e.g., sum of all the got-ups (when user gets out of bed) detected during the different sleep periods).

The “REM sleep” contributor may refer to a sum total of REM sleep durations across all sleep periods of the sleep day including REM sleep. Similarly, the “deep sleep” contributor may refer to a sum total of deep sleep durations across all sleep periods of the sleep day including deep sleep. The “latency” contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the “timing” contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The “sleep” contributor may refer to the combined Sleep Score of all sleep periods within the sleep day. The “sleep balance” contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The “resting heart rate” contributor may indicate a lowest heart rate from the longest sleep period of the sleep day (e.g., primary sleep period) and/or the lowest heart rate from naps occurring after the primary sleep period.

Continuing with reference to the “contributors” (e.g., factors, contributing factors) of the Readiness Score, the “HRV balance” contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The “recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for determining a circadian rhythm chronotype. In particular, the respective components of the system 200 may be used classify, using a machine learning model, the physiological data from the wearable device 104 into a circadian rhythm chronotype based on receiving the physiological data (e.g., including continuous nighttime temperature data, activity data, sleep pattern data, or additional or alternative physiological parameters). The circadian rhythm chronotype for the user may be predicted by leveraging temperature sensors, heart rate sensors, and the like, on the ring 104 of the system 200.

The system 200 may compare the determined circadian rhythm chronotype to sleep pattern data from a night preceding the current calendar day. In such cases, the system 200 may display, to the user 102, a graphical representation of an averaging over a period of time (e.g., the last 90 days or some other configurable time period) of at least the sleep pattern data relative to the sleep pattern data from the night preceding the current calendar day.

For example, as noted previously herein, the ring 104 of the system 200 may be worn by a user 102 to collect physiological data from the user 102, including continuous nighttime temperature data, activity data, sleep pattern data, and the like. The ring 104 of the system 200 may collect the physiological data from the user 102 based on arterial blood flow, that may provide a more accurate measurement signal as compared to measuring venous blood flow. However, the concepts described herein may also be applicable to measurements taken from venous blood flow or some combination of arterial and venous blood flow.

The physiological data may be collected continuously. In some implementations, the processing module 230-*a* may sample the user's temperature continuously throughout the day and night. Sampling at a sufficient rate (e.g., one sample per minute) throughout the day may provide sufficient temperature data for analysis described herein. In some implementations, the ring 104 may continuously acquire temperature data, activity data, sleep pattern data, heart rate data, and the like (e.g., at a sampling rate). Data collected by the ring 104 may be used to determine a circadian rhythm chronotype. Examples of circadian rhythm chronotype determinations are further shown and described with reference to FIGS. 3 and 6.

Referring to the system 200 illustrated in FIG. 2, the ring 104 may be worn by a user 102 and may collect data associated with the user 102 throughout the day and night (e.g., continuously). The ring 104 may collect data (e.g., temperature, sleep, MET, heart rate) and transmit collected data to the user device 106. In some cases, the user device 106 may forward (e.g., relay, transmit) the data received from the ring 104 to the servers 110 for processing. Additionally, or alternatively, the user device 106 and/or the ring 104 may perform processing on the collected data.

Continuing with the same example, the ring 104, the user device 106, the servers 110, or any combination thereof, may determine the circadian rhythm chronotype based on the collected data. Upon determining the circadian rhythm chronotype, the servers 110 may transmit an indication of the circadian rhythm chronotype to the user device 106. Alternatively, in cases where the user device 106 performs data processing, the user device 106 may generate the indication of the determined circadian rhythm chronotype. In this example, the next time the user opens the wearable application 250, an indication of the determined circadian rhythm chronotype may be presented to the user via the GUI 275 of the user device 106. This process and some exemplary but non-limiting examples of a user interface are further described with reference to FIG. 8.

For the purposes of the present disclosure, the terms "circadian rhythm chronotype," "circadian chronotype," "circadian profile," and like terms, may be used interchangeably. In some cases, the system 100 (e.g., user device 106, server 110) may be configured to receive data collected from a user 102 via the ring 104, and determine the circadian rhythm chronotype.

Figure 3:
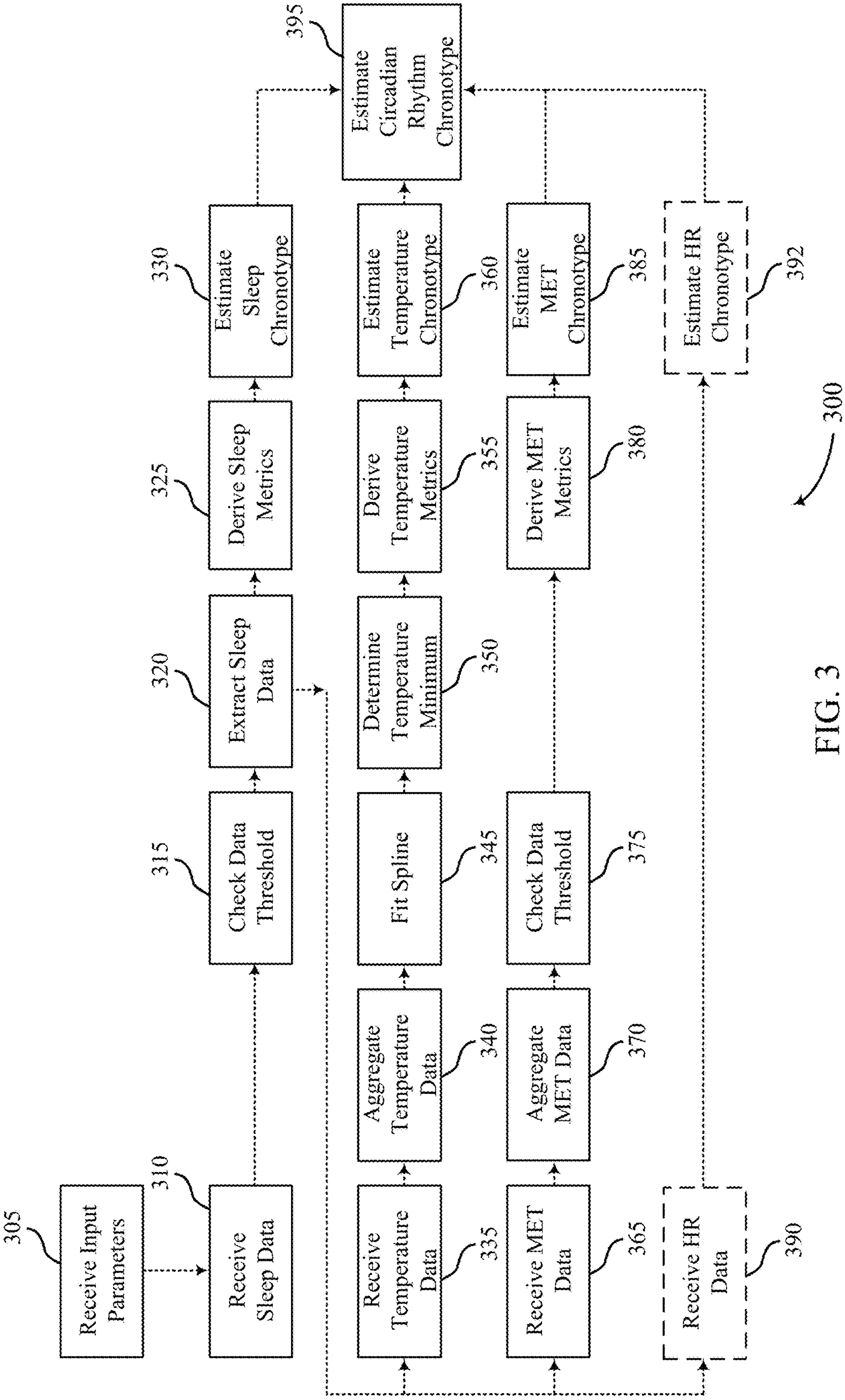
FIG. 3 shows an example of a system that supports techniques for determining a circadian rhythm chronotype in accordance with aspects of the present disclosure.

FIG. 3 shows an example of a system 300 that supports techniques for determining a circadian rhythm chronotype in accordance with aspects of the present disclosure. The system 300 may implement, or be implemented by, system 100, system 200, or both. In particular, system 300 illustrates an example of a ring 104 (e.g., wearable device 104), a user device 106, and a server 110, as described with reference to FIG. 1.

The system 300 may include an algorithm for chronotype characterization. In such cases, the system 300 may determine a circadian rhythm chronotype from one or more sources of data. As further described herein, if the system 300 receives an amount of data that satisfies a threshold, the system 300 may determine the circadian rhythm chronotype. If the system 300 determines that the amount of data fails to satisfy the threshold, the system 300 may refrain from determining the circadian rhythm chronotype. The system 300 may include one or more processing pipelines and a collective estimation for each processing pipeline. For example, the system 300 may classify each set of physiological data into different chronotypes (e.g., to determine whether a user is an "active person," or has a "regular sleep schedule," etc.). The system 300 may then determine the circadian rhythm chronotype based on classifying each set of physiological data.

At 305, the system 300 may receive input parameters. The input parameters may include a user identification (e.g., identity of user), a history length (e.g., a quantity of days that the system 300 receives data), a timeline (e.g., a start date of receiving physiological data and an end date of receiving physiological data), configuration parameters, data thresholds, or a combination thereof.

At 310, the system 300 may receive sleep data. For example, the system 300 may receive physiological data associated with a user from a wearable device for a period of time. The physiological data may include at least sleep pattern data. In some cases, the sleep pattern data may include sleep regularity data. In such cases, the system 300 may load sleep summary data (e.g., sleep data, sleep pattern data, or both) within the timeframe (e.g., the period of time) and process the sleep summary data. In some examples, sleep pattern data may include at least a time that a user goes to sleep each night (or goes to bed but has not yet fallen asleep) and a time that the user wakes up in the morning.

At 315, the system 300 may check a data threshold. For example, the system 300 may determine whether a quantity of received sleep data satisfies a threshold. The system 300 may determine that the quantity of received sleep data fails to satisfy the threshold. In such cases, the system 300 may refrain from extracting sleep data. For example, the system 300 may determine that system 300 does not include a sufficient amount of data to estimate the sleep chronotype. In other examples, the system 300 may determine that the quantity of received sleep data satisfies (e.g., is equal to or exceeds) the threshold.

The threshold may be an example of the history length that indicates the quantity of days that the system 300 receives the sleep data. In such cases, the threshold may be predetermined in that the system 300 receives the threshold at 305 prior to receiving the sleep data at 310. The system 300 may identify the history length to determine whether the quantity of received sleep data satisfies the threshold. In some examples, the threshold may be 90 consecutive nights in a same time zone. However, this threshold may be configured and/or changed over time by a user or the system 300.

At 320, the system 300 may extract sleep data. For example, the system 300 may discard sleep data that may be under the influence of jet lag (e.g., across two or more time zones). The system 300 may extract sleep data based on determining that the received sleep data includes minimal gaps between measurements (e.g., that the sleep data was received for 90 consecutive nights). In some cases, the system 300 may extract sleep data in response to checking the data threshold and determining that the data satisfies the threshold.

The system 300 may extract the last "n" (e.g., history length) long sleep data. In such cases, the system 300 may narrow down the subset of sleep data (e.g., including the measurements dates) with which to proceed. For example, the system 300 may extract sleep data measured during the history length (e.g., the period of time). Extracting the sleep data at 320 may trigger the data processing pipeline for the temperature data, the MET data, and/or the heart rate data, as described herein.

At 325, the system 300 may derive sleep metrics. For example, the system 300 may determine that the sleep data (e.g., the sleep pattern data) includes a wake time, a bedtime, a sleep duration, or a combination thereof. In such cases, the system 300 may identify the average wake time, average bedtime, average sleep duration, or a combination thereof for the user over the period of time. In some cases, the system 300 may determine a sleep regularity index based on receiving the physiological data (e.g., the sleep data).

At 330, the system 300 may estimate the sleep chronotype. For example, the system 300 may classify the physiological data from the wearable device into a chronotype associated with the sleep pattern data. In some cases, the system 300 may determine the sleep chronotype (e.g., the third chronotype as referred to elsewhere herein) based on determining the sleep regularity index. The system 300 may input the physiological data into a machine learning classifier. In such cases, the system 300 may use machine learning to classify the sleep chronotype, determine the circadian rhythm chronotype, or both.

At 335, the system 300 may receive temperature data. For example, the system 300 may receive physiological data associated with a user from a wearable device for a period of time. The physiological data may include at least continuous nighttime temperature data, continuous daytime temperature data, or both. In such cases, the system 300 may load continuous nighttime temperature data within the timeframe (e.g., the period of time) and process the continuous nighttime temperature data. The continuous nighttime temperature data may be loaded and processed based on extracting sleep data. For example, the system 300 filters down the data according to the narrowed (e.g., extracted) sleep times. In such cases, the system 300 may discard the daytime temperature data and store the nighttime temperature data.

At 340, the system 300 may aggregate temperature data. For example, the system 300 may determine the aggregated time series by calculating the 75th percentile of the data points measured at a same time of day for different days. In such cases, the system 300 may determine the aggregated sleep temperature. For example, the system 300 may generate a pool of measured values (e.g., including the temperature value and time stamp of the temperature value) over the course of weeks or months of sleep data. In some cases, the system 300 may discard temperature values for nightly spikes and/or baseline changes that may indicate outliers compared to the rest of the temperature data. In some examples, the system 300 may record the continuous nighttime temperature data for the last 90 nights of sleep data.

The temperature time series may be filtered to contain data that may be measured during bedtime. The system 300 may quantize the nighttime temperature data into minute by minute bins and gather all the temperature values that were recorded in each minute-long bin. In such cases, the system 300 may aggregate a distribution of temperature values per minute and extract out the 75th percentile of every minute-long bin distribution. The 75th percentile of each bin may create a time series that may represent the aggregated temperature signal and the overall temperature variation over the 90 consecutive nights, that may be further described with respect to FIG. 4.

The system 300 may assign the 75th percentile of each bin (e.g., a minute-long interval) as a representative temperature in that bin in case there is a temperature value measured in at least 20% of the underlying nights. The number of values in each bin may be stored as a weight for the representative value. In some cases, the first half an hour of the aggregated temperature signal may be omitted in the calculations that the temperature is stabilizing and thus making an upward rise for many users. In such cases, discarding the first half an hour part of temperature values may prevent issues with fitting a function to the data such as spline fitting distortion.

At 345, the system 300 may fit a spline (or other mathematical function) on the aggregated sleep temperature. For example, the system 300 may fit a 5th degree univariate spline on the aggregated temperature signal with the derived weights (e.g., the number of values in each minute-long interval and/or bin). In such cases, the system 300 may fit a spline to the time series. The system 300 may fit the spline in response to aggregating the temperature data.

At 350, a temperature minimum may be determined. The temperature minimum may be determined based on fitting a spline on the aggregated sleep temperature. In such cases, the temperature minimum may include a time of the temperature minimum and a value of the temperature minimum. For example, the system 300 may identify a time of night associated with a nighttime temperature minimum based on receiving the physiological data. To determine the minimum temperature value, the system 300 may determine whether 90 percent of the spline fit values are larger than the local minimum value. In some cases, the system 300 may determine the maximum and/or minimum temperature value. In some cases, the system 300 may identify more than one minimum temperature value. In such cases, the system 300 may select the lowest minimum temperature value.

If the system 300 is unable to determine a temperature minimum, the system 300 may refrain from deriving temperature metrics. The system 300 may be unable to estimate the temperature chronotype if the temperature minimum is not determined. In some cases, the system 300 may determine if a difference between the 95th percentile and the 5th percentile of the aggregated temperature signal satisfies a threshold. In cases where the difference satisfies the threshold, the system 300 may derive temperature metrics. If the system 300 determines that the difference fails to satisfy the threshold, the system 300 may refrain from deriving temperature metrics.

At 355, the system 300 may derive temperature metrics. For example, the system 300 may derive temperature metrics in response to determining a temperature minimum. At 360, the system 300 may estimate the temperature chronotype. For example, the system 300 may classify the physiological data from the wearable device into a first chronotype associated with the continuous nighttime temperature data. In some cases, classifying the physiological data into the first chronotype associated with the continuous nighttime temperature data may be in response to identifying the time of night associated with the nighttime temperature minimum. The system 300 may input the temperature data into a machine learning classifier. In such cases, the system 300 may use machine learning to classify the temperature chronotype, determine the circadian rhythm chronotype, or both. In some cases, the system 300 may classify the physiological data from the wearable device into a first chronotype associated with the continuous nighttime temperature data, sleep pattern data, activity data, or a combination thereof.

At 365, the system 300 may receive MET data. For example, the system 300 may receive physiological data associated with a user from a wearable device for a period of time. The physiological data may include at least activity data. In such cases, the system 300 may load the MET data and process the MET data. The MET data may be loaded and processed based on extracting the sleep data.

At 370, the system 300 may aggregate MET data. At 375, the system 300 may check a data threshold. For example, the system 300 may determine whether a quantity of received MET data satisfies a threshold. The system 300 may determine that the quantity of received MET data fails to satisfy the threshold. In such cases, the system 300 may refrain from deriving MET metrics. For example, the system 300 may determine that system 300 does not include a threshold amount of data to estimate the MET chronotype. In other examples, the system 300 may determine that the quantity of received MET data satisfies (e.g., is equal to or exceeds) the threshold.

The threshold may be an example of the history length that indicates the quantity of days that the system 300 receives the MET data. In such cases, the threshold may be predetermined such that the system 300 receives the threshold at 305 prior to receiving the MET data at 365. The system 300 may identify the history length to determine whether the quantity of received MET satisfies the threshold. In some examples, the threshold may be 90 consecutive days in a same time zone. At 380, the system 300 may derive MET metrics. For example, the system 300 may derive MET metrics in response to determining that the MET data satisfies the threshold.

At 385, the system 300 may estimate the MET chronotype. For example, the system 300 may classify the physiological data from the wearable device into a second chronotype associated with the activity data. The system 300 may input the MET data into a machine learning classifier. In such cases, the system 300 may use machine learning to classify the MET chronotype, determine the circadian rhythm chronotype, or both.

At 390, the system 300 may receive heart rate data. For example, the system 300 may receive physiological data associated with a user from a wearable device for a period of time. The physiological data may include at least heart rate data. In such cases, the system 300 may load the heart rate data and process the heart rate data. The heart rate data may be loaded and processed based on extracting the sleep data.

At 392, the system 300 may estimate the heart rate chronotype. For example, the system 300 may classify the physiological data from the wearable device into a fourth chronotype associated with the heart rate data in response to receiving the physiological data. In such cases, the system 300 may receive heart rate data and use the heart rate data to determine the heart rate chronotype.

At 395, the system 300 may determine the circadian rhythm chronotype based on the continuous nighttime temperature data and the first chronotype, the second chronotype, and the third chronotype. In some examples, the system 300 may determine the circadian rhythm chronotype based on the continuous nighttime temperature data, the first chronotype, the second chronotype, the third chronotype, or a combination thereof. For example, the system 300 may determine the circadian rhythm chronotype based on the continuous nighttime temperature data and in response to determining the sleep chronotype, the temperature chronotype, the MET chronotype, the heart rate chronotype, or a combination thereof. In some cases, the circadian rhythm chronotype may be determined in response to inputting the physiological data into the machine learning classifier.

The system 300 may determine the circadian rhythm chronotype based on a quantity of measured sleep data satisfying the threshold within the period of time. In such cases, the system 300 may determine the circadian rhythm chronotype based on the sleep summary data and at least an estimation of a sleep, temperature, and/or MET chronotype. The system 300 may fuse the estimations derived from the different sources into one collective estimated chronotype for the circadian rhythm chronotype. As such, by enabling more complete and accurate circadian rhythm chronotype determination, techniques described herein may enable the system 300 to provide improved insights and guidance to the user that better correlate to the user's overall health.

Figure 4:
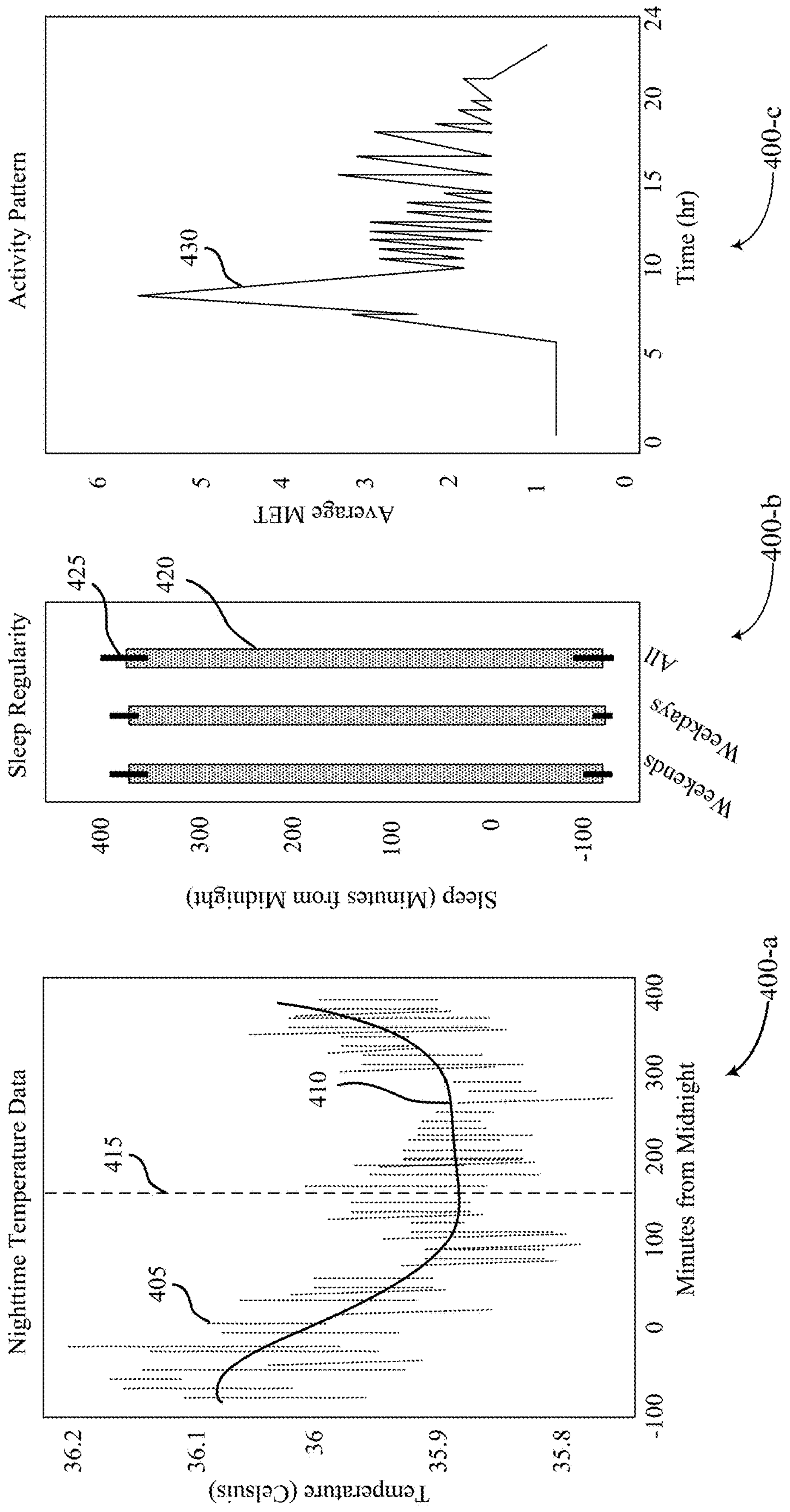
FIG. 4 shows an example of timing diagrams that supports techniques for determining a circadian rhythm chronotype in accordance with aspects of the present disclosure.

FIG. 4 shows an example of timing diagrams 400 that supports techniques for determining a circadian rhythm chronotype in accordance with aspects of the present disclosure. The timing diagram 400 may implement, or be implemented by, aspects of the system 100, system 200, system 300, or a combination thereof. For example, in some implementations, the timing diagrams 400 may be displayed to a user 102 via the GUI 275 of the user device 106, as shown in FIG. 2.

As described in further detail herein, the system may be configured to determine a circadian rhythm chronotype. In some cases, the user's core body temperature pattern throughout the night may be an indicator that may characterize the chronotype of users. For example, skin temperature during the night and the sleep timeline may determine a temperature chronotype. As such, the timing diagram 400-*a* illustrates a relationship between a user's temperature data and a time duration from midnight (e.g., minutes from midnight). In this regard, the plurality of dashed vertical lines illustrated in the timing diagram 400-*a* may be understood to refer to the "aggregated temperature data 405," as described with reference to block 340 in FIG. 3. In this regard, the solid curved line illustrated in the timing diagram 400-*a* may be understood to refer to the "fitted spline 410," as described with reference to block 345 in FIG. 3. In this regard, the single dashed vertical line in the timing diagram 400-*a* may be referred to as the "temperature minimum 415," as described with reference to block 350 in FIG. 3.

In some cases, the system may determine, or estimate, the temperature minimum 415 for a user based on the continuous nighttime temperature data for the user collected via the ring. In some implementations, the system may determine the temperature chronotype, the circadian rhythm chronotype, or both in response to receiving the continuous nighttime skin temperature data. The skin temperature data may be collected at one-minute increments (e.g., frequency).

In some cases, the system (e.g., ring, user device, server) may receive physiological data associated with the user from a wearable device. The physiological data may include at least temperature data and also may include heart rate data along with other physiological measurements or derived values. The temperature data may be continuously collected by the wearable device. The physiological measurements may be taken continuously throughout the day and/or night. For example, in some implementations, the ring may be configured to acquire physiological data (e.g., temperature data, sleep data, heart rate, MET data, and the like) continuously in accordance with one or more measurement periodicities throughout the entirety of each day/sleep day. In other words, the ring may continuously acquire physiological data from the user without regard to "trigger conditions" for performing such measurements. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body or if the user were manually taking their temperature once per day.

The timing diagram 400-*a* shown in FIG. 4 illustrates a relative timing of the nighttime temperature minimum 415 related to minutes from midnight. For example, the nighttime temperature minimum may be a value of about 35.9 degrees Celsius at 150 minutes after midnight (e.g., 2:30 AM). In some cases, the temperature chronotype may be determined based on a time of night associated with a nighttime temperature minimum 415. For example, a temperature chronotype that characterizes the user as a "morning type" user may include a nighttime temperature minimum 415 at a mid-sleep point whereas a temperature chronotype that characterizes the user as an "evening type" user may include a nighttime temperature minimum 415 at the latter half of the user's sleep (e.g., after the mid-sleep point). In some cases, the difference between a time of night for the temperature minimum 415 for "morning type" users and "evening type" users may be two hours.

The system may use the aggregated temperature data 405 time series to fit a spline 410 to the aggregated temperature data 405. In such cases, the system may use the aggregated temperature data 405 to characterize the fitted spline 410 into different categories. For example, the timing diagram 400-*a* shown in FIG. 4 illustrates a u-shaped fitted spline 410. The u-shaped fitted spline 410 may illustrate that the aggregated temperature data 405 decreases, reaches a minimum (e.g., temperature minimum 415), and increases before the wake time.

In other examples, the fitted spline 410 may include a constant downward slope. In such cases, the aggregated temperature data 405 may constantly follow a downward trend throughout the night. In other examples, the fitted spline 410 may include a constant upward slope throughout the night.

In some examples, the system may determine that the temperature data received fails to satisfy a threshold. In such cases, the system may identify the users as "rare syncers" where the system may not receive enough temperature data to determine the aggregated temperature data 405, the fitted spline 410, the temperature minimum 415, or a combination thereof. In some cases, a cluster of the user's aggregated temperature data 405 may occur in a tight (e.g., narrow) range such that the ups and down of the time series (e.g., aggregated temperature data 405) may include less accuracy and reliability. The tight range may be an example of minimum temperature variation along the y-axis. In such cases, the system may discard the temperature data and refrain from using the temperature data to determine the circadian rhythm chronotype.

The timing diagram 400-*b* shown in FIG. 4 illustrates a relative timing of the sleep regularity relative to weekends, weekdays, and both. For example, the timing diagram 400-*b* illustrates a relationship between a user's sleep and a day of the week. In this regard, the dotted bars illustrated in the timing diagram 400-*b* may be understood to refer to the "sleep duration 420." The sleep duration 420 may include a wake time, a bedtime, a sleep duration, or a combination thereof. In this regard, the black bars illustrated in the timing diagram 400-*b* may be understood to refer to the "interquartile range 425." In some cases, the system may determine, or estimate, the sleep chronotype, the circadian rhythm chronotype, or both based on the sleep pattern data.

The system may use the sleep pattern data to characterize the users into different categories (e.g., sleep chronotypes). For example, the timing diagram 400-*b* shown in FIG. 4 illustrates regular sleepers. In such cases, the sleep duration 420 for the weekends and weekdays may be consistent between the weekend and weekdays to indicate the user wakes up at the same (e.g., consistent) time every day and goes to bed at the same (e.g., consistent) time every day. For example, a bottom of the sleep duration 420 for the weekends may be aligned with a bottom of the sleep duration 420 for the weekdays. A top of the sleep duration 420 for the weekends may be aligned with a top of the sleep duration 420 for the weekdays. The wake time may be illustrated as the top of the sleep duration 420, and the bedtime may be illustrated as the bottom of the sleep duration 420. The interquartile ranges 425 may represent the volatility of the variation for the sleep data across the period of time. In such cases, a shorter interquartile range 425 may indicate less variation of the bedtimes and wake times while a longer interquartile range 425 may indicate more variation of the bedtimes and wake times.

In some cases, the timing diagram may illustrate irregular sleepers. In such cases, the sleep duration 420 for the weekends and weekdays may be inconsistent between the weekend and weekdays to indicate the user wakes up at different times for the weekends and/or weekdays and goes to bed different times for the weekends and/or weekdays. For example, the bottom of the sleep duration 420 for the weekends may be misaligned with (e.g., longer or shorter than) the bottom of the sleep duration 420 for the weekdays. The top of the sleep duration 420 for the weekends may be misaligned with (e.g., longer or shorter than) the top of the sleep duration 420 for the weekdays. In such cases, an interquartile range 425 may be longer than the interquartile range 425 as illustrated in timing diagram 400-*b* such that the interquartile range 425 indicates a higher variability of sleep pattern data.

In some cases, the timing diagram may illustrate irregular sleepers. In such cases, the sleep duration 420 for the weekdays may be shorter than the sleep duration for the weekends. For example, the timing diagram may indicate that the user accumulates sleep debt over the course of the weekdays and sleeps longer during the weekends. For example, the bottom and top of the sleep duration 420 for the weekdays may be misaligned with (e.g., shorter than) the bottom and top, respectively, of the sleep duration 420 for the weekends. In such cases, an interquartile range 425 may be shorter such that the interquartile range 425 indicates a smaller variability of sleep pattern data between the weekends and the weekdays.

In some cases, the system may determine a sleep regularity index. The sleep regularity index may indicate how uniformly a user sleeps. In some cases, the sleep regularity index may take into account naps logged by the user or received by the system. In some examples, irregular bed and wake times may be associated with increased risk of different diseases. The sleep regularity index may measure the consistency of a user's sleep timeline such that users who frequently change their sleep timing and their pattern of light/dark exposure may experience misalignment between the circadian system and the sleep/wake cycle. Irregular sleep may decrease a user's daily performance and cognitive functions, and is associated with health threatening risk factors. In such cases, having a regular sleep pattern may be beneficial to the overall health of the user. In some cases, compliance with a user's established sleep pattern may be a contributing factor to the user's sleep quality and thus also to their Sleep Score and Readiness Score.

The timing diagram 400-*c* shown in FIG. 4 illustrates a relative timing of the activity pattern related to a time of day for a single calendar day. For example, the timing diagram 400-*c* illustrates a relationship between a user's average MET and a time of day. In this regard, the solid line illustrated in the timing diagram 400-*c* may be understood to refer to the "activity data 430." In some cases, the system may determine, or estimate, the MET chronotype, the circadian rhythm chronotype, or both based on the activity data 430.

The system may use the quantity of average MET (e.g., activity data 430) and the time of day associated with the average MET to characterize the users into different categories (e.g., activity chronotypes). For example, the timing diagram 400-*c* shown in FIG. 4 illustrates morning active users. The aggregated MET time series (e.g., activity data 430) may illustrate how active a user has been throughout the course of a day within the period of time. The peak of activity data 430 is before 10:00 AM, thereby indicating that the user is a morning active user.

In other examples, the activity data 430 may illustrate how the user is an evening active user. In such cases, the activity data 430 may include lower MET values in the morning with an increase in MET values as the day continues. For example the peak of activity data 430 may be during the evening. In some cases, the activity data 430 may illustrate how the user is a non-active user. In such cases, the activity data 430 may be constant (e.g., stable) through the day. For example, the average MET values may be low and the same throughout the day (e.g., a horizontal line along the x-axis).

In some examples, the activity data 430 may illustrate how users may be active at specific times of day. For example, the activity data 430 may include one or more distinguishable peaks throughout the day. In some cases, a single, distinguishable peak may indicate that the user is active at a very specific time on a regular basis (e.g., at the same time over the course of more than one day, week, month, etc.). In other examples, a peak with a wider bandwidth and lower amplitude may indicate that the user is active within a timeframe over a duration of time on a regular basis.

In some examples, the system may determine that the activity data 430 received fails to satisfy a threshold. In such cases, the system may identify the users as "non-permanent wearers" or "nighttime wearers" where the system may not receive enough activity data 430 to determine the activity chronotype. For example, the activity data 430 may be unavailable or partially unavailable during the daytime. In such cases, the system may discard the activity data 430 and refrain from using the activity data 430 to determine the circadian rhythm chronotype.

Figure 5:
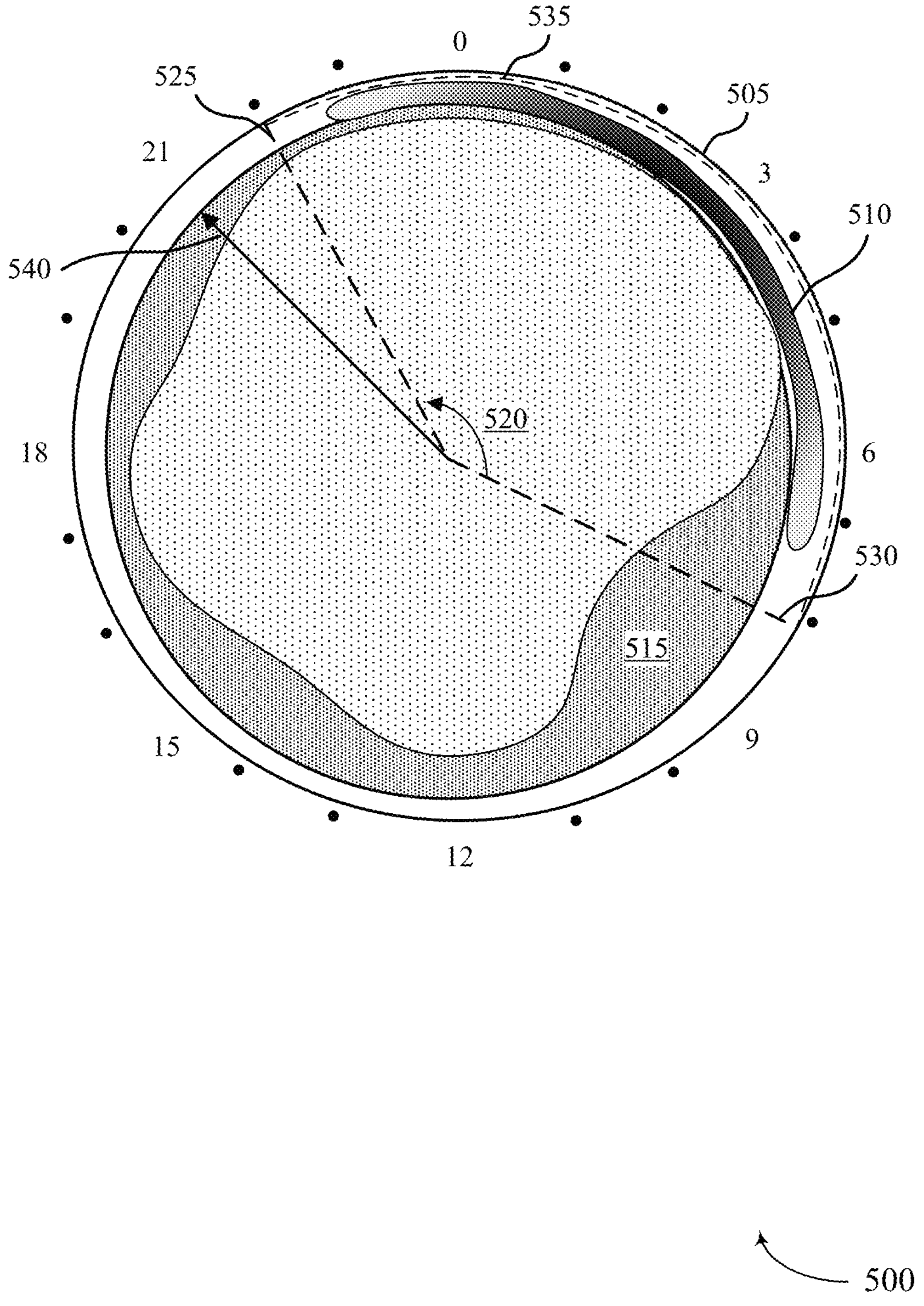
FIG. 5 shows an example of a graphical representation that supports techniques for determining a circadian rhythm chronotype in accordance with aspects of the present disclosure.

FIG. 5 shows an example of a graphical representation 500 that supports techniques for determining a circadian rhythm chronotype in accordance with aspects of the present disclosure. The graphical representation 500 may implement, or be implemented by, aspects of the system 100, system 200, system 300, timing diagrams 400, or any combination thereof. For example, the graphical representation 500 may be displayed on a GUI 275 of a user device 106 (e.g., user device 106-*a*, 106-*b*, 106-*c*) corresponding to a user 102.

The graphical representation 500 may include a circular representation 505 of a twenty-four hour timespan. For example, the system may overlay one or more physiological parameters or an aggregation or characterization of one or more physiological parameters onto the twenty-four hour timespan. In one non-limiting example, the system may overlay an averaging over a period of time (e.g., the last 60 or 90 days) of at least continuous nighttime temperature data, activity data, sleep pattern data, or some combination or subset of this data, against the circular representation 505 of a twenty-four hour timespan. In some cases, the circular representation 505 may include other shapes such as a rectangular, oval, triangular, and the like.

In some cases, the graphical representation 500 may include a first segment 510, a second segment 515, and a third segment 520. The first segment 510 may include the averaging over the period of time of the continuous nighttime temperature data. In such cases, the system 200 may cause the GUI 275 of the user device to display a first segment 510 of the circular representation 505 of the twenty-four hour timespan that includes the averaging over the period of time of the continuous nighttime temperature data. In some examples, the first segment 510 may include an arch-shaped segment that represents the averaging over the period of time of the continuous nighttime temperature data as a colored gradient that indicates variations in nighttime temperature throughout a duration of sleep.

For example, the continuous nighttime temperature may be included in an outermost circular line with a colored gradient. The colored gradient may be an example of a red-blue gradient in which the segments of red indicate a higher nighttime temperature than the segments of blue, that indicate a lower nighttime temperature. For example, the segments of red may be displayed towards the center of the first segment 510 while the segments of blue may be displayed towards the ends of the first segment 510 in users that experience higher nighttime temperatures towards the middle of the night. In other examples, the colored gradient may be an example of a blue gradient in which the segments of darker blue indicate a lower nighttime temperature than the segments of lighter blue, that indicate a higher nighttime temperature. For example, the segments of darker blue may be displayed towards the center of the first segment 510 while the segments of lighter blue may be displayed towards the ends of the first segment 510. In such cases, the colored gradient of the first segment 510 may allow the user to quickly and effectively identify a time of night that the lowest nighttime temperature occurs. The time and value of the lowest nighttime temperature may indicate whether the user is a morning person or an evening person. The first segment 510 may include an average of the continuous nighttime temperature data for the past 30 days, 60 days, or 90 days, or some other configurable time period, including weekends and weekdays.

In some cases, the second segment 515 may include the averaging over the period of time of the activity data. In such cases, the system 200 may cause the GUI 275 of the user device to display a second segment 515 of the circular representation 505 of the twenty-four hour timespan that includes the averaging over the period of time of the activity data. In some examples, the second segment 515 may include a curve-shaped segment that represents the averaging over the period of time of the activity data as a graphical plot that indicates relative changes in activity level over the twenty-four hour timespan.

For example, the graphical representation 500 may include activity tracking. For users with activity at regular times of the day, the second segment 515 may include a definitive shape. For example, the second segment 515 may not be visible to the user during the hours that the user sleeps, thereby indicating the user is not active during the nighttime hours. As illustrated in FIG. 5, the second segment 515 may indicate that the user is active in the morning (e.g., between 8:00-9:00 AM) such that the second segment 515 may be most visible during the morning hours. The second segment 515 may extend from the outer circumference of the circular representation 505 and inwards toward the center of the circular representation 505. In some cases, the second segment 515 may be displayed during the evening hours, thereby indicating that the user is active during the evening hours. The shape volume of the second segment 515 may be associated with the amount of activity. For example, the greater volume of the second segment 515 may indicate that the user is more active than other periods of time throughout the day. The second segment 515 may include an average of the activity data for the past 30 days, 60 days, or 90 days, or some other configurable period of time, including weekends and weekdays.

In some cases, the third segment 520 may include the averaging over the period of time of the sleep pattern data. In such cases, the system 200 may cause the GUI 275 of the user device to display the third segment 520 of the circular representation 505 of the twenty-four hour timespan that includes the averaging over the period of time of the sleep pattern data. In some examples, the third segment 520 may include a wedge-shaped segment that represents the averaging over the period of time of the sleep pattern data. The third segment 520 may include a first side 525 indicating a time the user goes to sleep, a second side 530 indicating a time the user wakes up, and a third curved side 535 that is adjacent to the circular representation 505 of the twenty-four hour timespan. In such cases, the third segment 520 may indicate a bedtime, a wake time, a sleep duration, or a combination thereof.

For example, the graphical representation 500 may indicate that the user goes to sleep at 10:00 PM and wakes up at 8:00 AM. The crispness of the first side 525 and the second side 530 may indicate the regularity of the sleep data. For example, if the first side 525 and/or the second side 530 includes lines that are faint or less visible, this may be a visual indication that the user has irregular bedtimes, wake times, or both. In other examples, if the first side 525 and/or the second side 530 includes lines that are clear or visible or distinct, this may be a visual indication that the user has regular bedtimes, wake times, or both. The third segment 520 may include an average of the sleep pattern data for the past 30 days, 60 days, or 90 days, or some other configurable period of time, including weekends and weekdays.

In some examples, the graphical representation 500 may include one or more parameters 540. For example, the one or more parameters 540 may be an example of an indication of the current time of day. In other examples, the one or more parameters 540 may be an example of a message or an alert indicating heart rate data, an indication of a menstrual cycle, respiratory data, or a combination thereof. In such cases, the system may cause the GUI 275 of the user device to display one or more parameters 540 against the circular representation 505 of a twenty-four hour timespan that includes the averaging over the period of time of the heart rate data, an indication of a menstrual cycle, respiratory data, or a combination thereof. In some cases, the one or more parameters 540 may overlay the graphical representation 500 against the circular representation 505 of a twenty-four hour timespan.

The graphical representation 500 may allow the user to visualize their long term habits on a twenty-four hour clock user interface component. The graphical representation 500 may indicate a user's bedtime and wake-up times, nighttime temperatures, and activity data. In such cases, the system may provide insights to the user on key variables that factor into determining the circadian profile (e.g., circadian rhythm chronotype). The graphical representation 500 may be an example of a generated report to display a picture of the user's body clock changes, seasonal variations, the effects of travel, lifestyle habits, or a combination thereof.

In some cases, the graphical representation 500 may include a static rendering. By applying a smoothing function to the activity data (e.g., second segment 515), and obfuscating the exact borders of a user's bedtime and wake time (e.g., first side 525 and second side 530, respectively, of third segment 520), the system may display to the user an interactive and helpful tool to give insight into the user's lifestyle. The patterns determined from the bio signals (e.g., physiological data) received may classify the user into a number of categories including, for example, but not limited to, morning people, evening people, highly active people, inactive people, or a combination thereof. In such cases, the graphical representation 500 may classify the users as users who are well-aligned with their circadian rhythm chronotype and users who are ill-aligned with their circadian rhythm chronotype.

Figure 6:
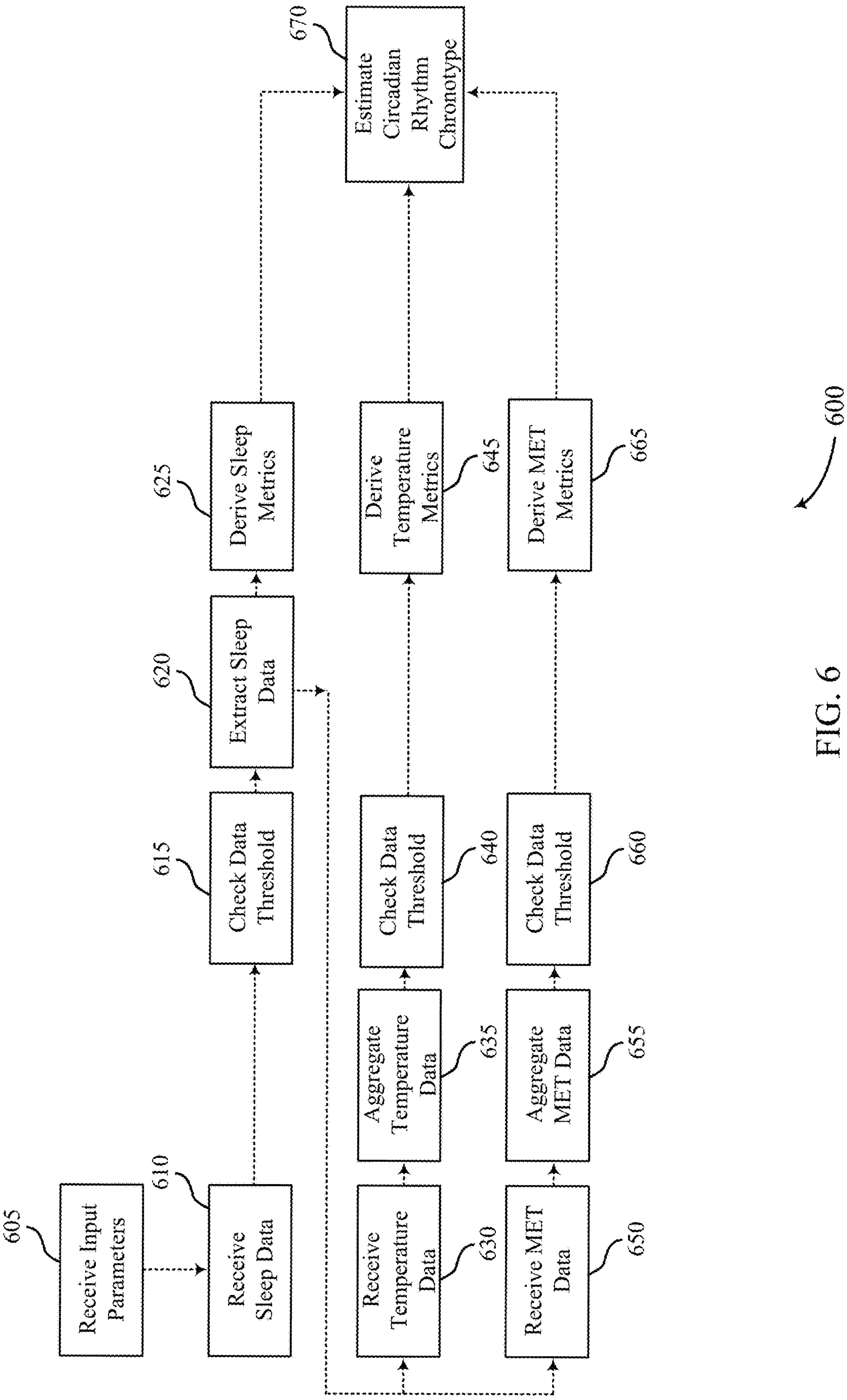
FIG. 6 shows an example of a system that supports techniques for determining a circadian rhythm chronotype in accordance with aspects of the present disclosure.

FIG. 6 shows an example of a system 600 that supports techniques for determining a circadian rhythm chronotype in accordance with aspects of the present disclosure. The system 600 may implement, or be implemented by, system 100, system 200, system 300, or a combination thereof. In particular, system 600 illustrates an example of a ring 104 (e.g., wearable device 104), a user device 106, and a server 110, as described with reference to FIG. 1.

The system 600 may include an algorithm for chronotype characterization. In such cases, the system 600 may determine a circadian rhythm chronotype from one or more sources of data. As further described herein, if the system 600 receives an amount of data that satisfies a threshold, the system 600 may determine the circadian rhythm chronotype. If the system 600 determines that the amount of data fails to satisfy the threshold, the system 600 may refrain from determining the circadian rhythm chronotype. The system 600 may include one or more processing pipelines and a collective estimation for each processing pipeline.

At 605, the system 600 may receive input parameters. The input parameters may include a user identification (e.g., identity of user), a history length (e.g., a quantity of days that the system 600 receives data), a timeline (e.g., a start date of receiving physiological data and an end date of receiving physiological data), configuration parameters, data thresholds, or a combination thereof.

At 610, the system 600 may receive sleep data. For example, the system 600 may receive physiological data associated with a user from a wearable device for a period of time. The period of time may be an example of 90 consecutive calendar days. The physiological data may include at least sleep pattern data. In some cases, the sleep pattern data may include sleep regularity data. In such cases, the system 600 may load sleep summary data (e.g., sleep data, sleep pattern data, or both) within the timeframe (e.g., the period of time) and process the sleep summary data. In some examples, sleep pattern data may include at least a time that a user goes to sleep each night (or goes to bed but has not yet fallen asleep), a time that the user wakes up in the morning, a sleep duration, or a combination thereof.

For example, the system 600 may receive, from the wearable device a first set of physiological data measured from the user by the wearable device that is collected over the period of time. The first set of the physiological data may include at least the sleep data. In some examples, the system 600 may receive, from the wearable device, a second set of physiological data measured from the user by the wearable device collected over a previous sleep day. For example, the second set of physiological data may include sleep pattern data from the previous night. In such cases, the previous night may be an example of the night immediately preceding the current calendar day. In some examples, the sleep data of the first set physiological data and the second set of physiological data may include sleep data derived from naps taken throughout one or more calendar days. For example, the first set of physiological data may include sleep data from naps measured over the period of time (e.g., 90 consecutive calendar days). The second set of physiological data may include sleep data from naps measured over the previous calendar day immediately preceding the current calendar day.

At 615, the system 600 may check a data threshold. For example, the system 600 may determine whether a quantity of received sleep data satisfies a threshold. The system 600 may determine that the quantity of received sleep data satisfies (e.g., is equal to or exceeds) the threshold. In other examples, the system 600 may determine that the quantity of received sleep data fails to satisfy the threshold. In such cases, the system 600 may refrain from extracting sleep data. The system 600 may determine that system 600 does not include a sufficient amount of data to estimate the circadian rhythm chronotype. For example, the system 600 may determine that the wearable device may be worn infrequently within the period of time, that the wearable device receives less than 30 instances of sleep measurements within the period of time, that the wearable device is worn partially during sleep, that the wearable device fails to sync, that high-frequency data is overwritten, that the user moved across different time zones such that the system 600 may not gather enough data within a same time zone, or a combination thereof.

The threshold may be an example of the history length that indicates the quantity of days that the system 600 receives the sleep data. In such cases, the threshold may be predetermined in that the system 600 receives the threshold at 605 prior to receiving the sleep data at 610. The system 600 may identify the history length to determine whether the quantity of received sleep data satisfies the threshold. In some examples, the threshold may be 90 consecutive nights in a same time zone, more than 30 instances of sleep measurements within the 90 consecutive nights, or both. However, this threshold may be configured and/or changed over time by a user or the system 600.

At 620, the system 600 may extract sleep data. For example, the system 600 may discard sleep data that may be under the influence of jet lag (e.g., across two or more time zones). In such cases, the system 600 may extract and discard sleep data that is measured in a time zone further than one hour from the most occurring time zone. The system 600 may extract sleep data based on determining that the received sleep data includes minimal gaps between measurements (e.g., that the sleep data was received for 90 consecutive nights). In some cases, the system 600 may extract sleep data in response to checking the data threshold and determining that the data satisfies the threshold.

The system 600 may extract the last "n" (e.g., history length) long sleep data. In such cases, the system 600 may narrow down the subset of sleep data (e.g., including the measurements dates) with which to proceed. For example, the system 600 may extract sleep data measured during the history length (e.g., the period of time). In some cases, the system 600 may extract and discard sleep data to avoid outliers of sleep data from affecting the circadian rhythm chronotype estimation. In other examples, the system 600 may extract the sleep data associated with sleep sessions that are longer than 3 hours and/or extract a single sleep session per calendar day. Extracting the sleep data at 620 may trigger the data processing pipeline for the temperature data, and/or the MET data, as described herein.

At 625, the system 600 may derive sleep metrics. For example, the system 600 may determine that the sleep data (e.g., the sleep pattern data) includes a wake time, a bedtime, a sleep duration, or a combination thereof. In such cases, the system 600 may identify the average wake time, average bedtime, average sleep duration, or a combination thereof for the user over the period of time.

In some examples, the system 600 may identify a median bedtime, a median wake time, a standard deviation of sleep midpoint, or a combination thereof. In such cases, the system 600 may process the sleep pattern data of the first set of physiological data to extract at least a standard deviation of a sleep midpoint, a median wake time wake that the user wakes up, a median bedtime that the user goes to sleep, or a combination thereof. For example, the system 600 may extract, from the sleep data, the median bedtime, the median wake time, the standard deviation of sleep midpoint, the average wake time, the average bedtime, the average sleep duration, or a combination thereof.

In some cases, the system 600 may input the first set of physiological data into the machine learning model. For example, the system 600 may input the sleep data, sleep metrics, extracted sleep data, or a combination thereof into the machine learning model The system 600 may classify, using the machine learning model, the first set of physiological data into the circadian rhythm chronotype in response to inputting the first set of physiological data into the machine learning model. For example, the system 600 may use the derived sleep metrics and a linear regression model to estimate the circadian rhythm chronotype, as described herein.

At 630, the system 600 may receive temperature data. For example, the system 600 may receive physiological data associated with a user from a wearable device for a period of time. The physiological data may include at least continuous nighttime temperature data, continuous daytime temperature data, or both. In such cases, the system 600 may load continuous nighttime temperature data within the timeframe (e.g., the period of time) and process the continuous nighttime temperature data. The continuous nighttime temperature data may be loaded and processed based on extracting sleep data. For example, the system 600 filters down the data according to the narrowed (e.g., extracted) sleep times. In such cases, the system 600 may discard the daytime temperature data and store the nighttime temperature data.

At 635, the system 600 may aggregate temperature data. For example, the system 600 may generate a pool of measured values (e.g., including the temperature value and time stamp of the temperature value) over the course of weeks or months of sleep data. In some cases, the system 600 may discard temperature values for nightly spikes and/or baseline changes that may indicate outliers compared to the rest of the temperature data. In some examples, the system 600 may record the continuous nighttime temperature data for the last 90 nights of sleep data. In such cases, the system 600 may record the temperature data that corresponds to the same calendar days that the sleep data was recorded (e.g., the 90 nights of sleep of data). The temperature time series may be filtered to contain data that may be measured during bedtime.

At 640, the system 600 may check a data threshold. For example, the system 600 may determine whether a quantity of received temperature data satisfies a threshold. In some examples, the system 600 may determine that the quantity of received temperature data satisfies (e.g., is equal to or exceeds) the threshold. The system 600 may determine that the quantity of received temperature data fails to satisfy the threshold. In such cases, the system 600 may refrain from deriving temperature metrics. For example, the system 600 may determine that system 600 does not include a sufficient amount of data to estimate the circadian rhythm chronotype.

In such cases, the system 600 may determine that the wearable device may be worn infrequently within the period of time, that the wearable device receives less than 30 instances of sleep measurements within the period of time, that the wearable device is worn partially during sleep, that the wearable device fails to sync, that high-frequency data is overwritten, that the user moved across different time zones such that the system 600 may not gather enough data within a same time zone, or a combination thereof. For example, if the high-frequency data is overwritten, skin temperature data may be missing from the received physiological parameters.

The threshold may be an example of the history length that indicates the quantity of days that the system 600 receives the temperature data. In such cases, the threshold may be predetermined in that the system 600 receives the threshold at 605 prior to receiving the temperature data at 630. The system 600 may identify the history length to determine whether the quantity of received temperature data satisfies the threshold. In some examples, the threshold may be 90 consecutive nights in a same time zone. However, this threshold may be configured and/or changed over time by a user or the system 600.

At 645, the system 600 may derive temperature metrics. For example, the system 600 may derive temperature metrics in response to checking the data threshold. The system 600 may process, by the application, the continuous nighttime temperature data to extract at least an average skin temperature, an average skin temperature for the five highest temperature values of a consecutive twenty-four hour timespan, an average skin temperature for the five lowest temperature values of a consecutive twenty-four hour timespan, or a combination thereof. For example, the system 600 may generate a daily temperature rhythm of the user to derive temperature metrics. In such cases, the system 600 may derive a time of day for the average skin temperature for the five highest temperature values in consecutive hours in a twenty-four hour time span, a time of day for the average skin temperature for the five lowest temperature values in consecutive hours in a twenty-four hour time span, an average skin temperature, or a combination thereof.

In some cases, the system 600 may input the temperature data, temperature metrics, extracted temperature data, or a combination thereof into the machine learning model. The system 600 may classify, using the machine learning model, the first set of physiological data into the circadian rhythm chronotype in response to inputting the first set of physiological data into the machine learning model. For example, the system 600 may use the derived temperature metrics and a linear regression model to estimate the circadian rhythm chronotype, as described herein.

At 650, the system 600 may receive MET data. For example, the system 600 may receive physiological data associated with a user from a wearable device for a period of time. The physiological data may include at least activity data. In such cases, the system 600 may load the MET data and process the MET data. The MET data may be loaded and processed based on extracting the sleep data.

At 655, the system 600 may aggregate MET data. At 660, the system 600 may check a data threshold. For example, the system 600 may determine whether a quantity of received MET data satisfies a threshold. The system 600 may determine that the quantity of received MET data satisfies (e.g., is equal to or exceeds) the threshold. In other examples, the system 600 may determine that the quantity of received MET data fails to satisfy the threshold. In such cases, the system 600 may refrain from deriving MET metrics. For example, the system 600 may determine that system 600 does not include a threshold amount of data to estimate the circadian rhythm chronotype.

In such cases, the system 600 may determine that system 600 does not include a sufficient amount of data to estimate the circadian rhythm chronotype. For example, the system 600 may determine that the wearable device may be worn infrequently within the period of time, that the wearable device receives less than 30 instances of sleep measurements within the period of time, that the wearable device is worn partially during sleep, that the wearable device fails to sync, that high-frequency data is overwritten, that the user moved across different time zones such that the system 600 may not gather enough data within a same time zone, or a combination thereof. Wearing the wearable device partially during sleep may result in missing MET data during the daytime. In such cases, the system 600 may refrain from extracting features from the MET data and/or physical activity data of the user during the day. If the wearable device is not synced frequently enough, the MET data may be missing from the received physiological data.

The threshold may be an example of the history length that indicates the quantity of days that the system 600 receives the MET data. In such cases, the threshold may be predetermined such that the system 600 receives the threshold at 605 prior to receiving the MET data at 650. The system 600 may identify the history length to determine whether the quantity of received MET satisfies the threshold. In some examples, the threshold may be 90 consecutive days in a same time The system 600 may record the MET data that includes the last 90 nights of sleep data. In such cases, the system 600 may record the MET data that corresponds to the same calendar days that the sleep data was recorded (e.g., the last 90 nights of sleep of data).

At 665, the system 600 may derive MET metrics. For example, the system 600 may derive MET metrics in response to determining that the MET data satisfies the threshold. The system 600 may process, by the application, the activity (e.g., MET) data of the first set of physiological data to extract at least an average MET value, a time that the user is active, or both. For example, the system 600 may compute a rest-activity rhythm and extract (e.g., derive) MET metrics. In such cases, the system 600 may extract, from the rest-activity rhythm, an average MET value for the ten most active consecutive hours in a twenty-four time span, an average MET value for the five least active consecutive hours in a twenty-four time span, a midpoint MET value for the ten most active consecutive hours in a twenty-four time span, a midpoint MET value for the five least active consecutive hours in a twenty-four time span, a time that maximum physical activity is measured, or a combination thereof.

In some cases, the system 600 may input the MET data, MET metrics, extracted MET data, or a combination thereof into the machine learning model. The system 600 may classify, using the machine learning model, the first set of physiological data into the circadian rhythm chronotype in response to inputting the first set of physiological data into the machine learning model. For example, the system 600 may use the derived MET metrics and a linear regression model to estimate the circadian rhythm chronotype, as described herein.

At 670, the system 600 may determine the circadian rhythm chronotype based on the sleep data, the temperature data, the MET data, or a combination thereof. In some examples, the system 600 may determine the circadian rhythm chronotype based on the derived metrics of sleep, temperature, MET, or a combination thereof. In some cases, the circadian rhythm chronotype may be determined in response to inputting the physiological data (e.g., the first set of physiological data) into the machine learning classifier.

In some cases, the system 600 may outputs a number between 16 to 86 that corresponds to the morningness-eveningness questionnaire (MEQ) score where 16 represents the most extreme evening type user and 86 represents the most extreme morning type user. The estimated MEQ score may be mapped to a midpoint of sleep. For example, in response to determining the estimated circadian rhythm chronotype, the system 600 may determine a midpoint of sleep for the user. The midpoint of sleep may be measured from midnight. The midpoint of sleep (e.g., including a sleep wake cycle) may be affected by the circadian rhythm chronotype. In such cases, the system 600 may determine the midpoint of sleep based on the user's circadian rhythm chronotype. In some cases, a midpoint of sleep for morning type users may have an earlier midpoint of sleep compared with a midpoint of sleep for the intermediate and evening type users.

The system 600 may determine a relationship between the MEQ score and the midpoint of sleep. For example, the system 600 may estimate the circadian rhythm chronotype and determine the relationship between the MEQ score and the midpoint of sleep in response to determining the circadian rhythm chronotype. In some cases, the relationship between the MEQ score and the midpoint of sleep may be linear. In such cases, the linear relationship may create a mapping to associate an optimal midpoint of sleep with each MEQ score.

The system 600 may determine the circadian rhythm chronotype based on a quantity of measured sleep data satisfying the threshold within the period of time. The system 600 may fuse the estimations derived from the different sources into one collective estimated chronotype for the circadian rhythm chronotype. As such, by enabling more complete and accurate circadian rhythm chronotype determination, techniques described herein may enable the system 600 to provide improved insights and guidance to the user that better correlate to the user's overall health.

Figure 7:
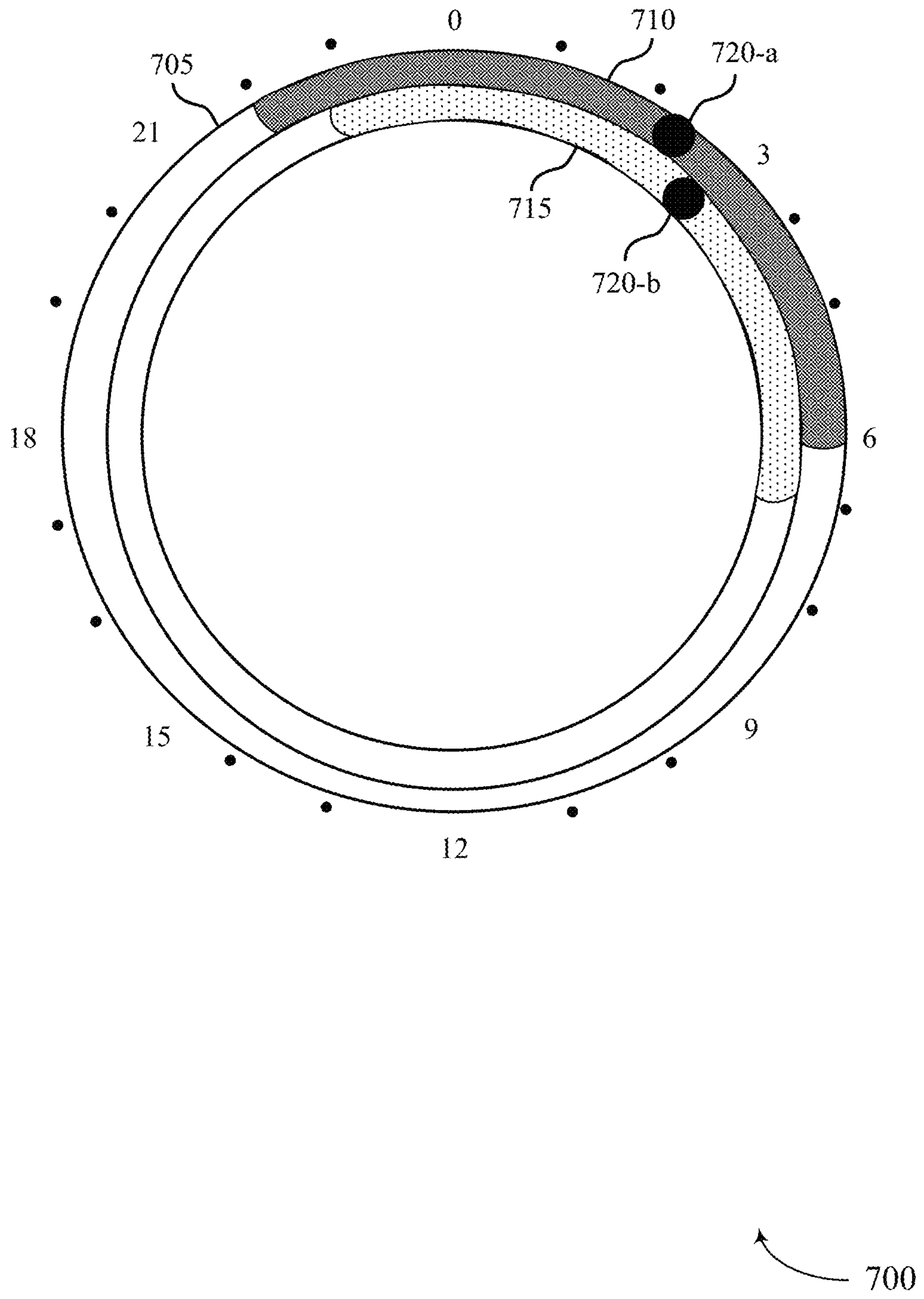
FIG. 7 shows an example of a graphical representation that supports techniques for determining a circadian rhythm chronotype in accordance with aspects of the present disclosure.

As described herein with reference to FIG. 7, the system 600 may compare the determined circadian rhythm chronotype and the received second set of physiological data (e.g., sleep data from the previous night). The system 600 may cause the GUI of the user device to display a message associated with the comparison, the determined circadian rhythm chronotype, the received second set of physiological data, or a combination thereof, as described with reference to FIG. 8.

FIG. 7 shows an example of a graphical representation 700 that supports techniques for determining a circadian rhythm chronotype in accordance with aspects of the present disclosure. The graphical representation 700 may implement, or be implemented by, aspects of the system 100, system 200, system 300, timing diagrams 400, system 600, or any combination thereof. For example, the graphical representation 700 may be displayed on a GUI 275 of a user device 106 (e.g., user device 106-*a*, 106-*b*, 106-*c*) corresponding to a user 102.

The graphical representation 700 may include a circular representation 705 of a twenty-four hour timespan. For example, the system may overlay one or more physiological parameters or an aggregation or characterization of one or more physiological parameters onto the twenty-four hour timespan. In one non-limiting example, the system may overlay the determined circadian rhythm chronotype and sleep data from the previous night's sleep against the circular representation 705 of a twenty-four hour timespan, as described with reference to FIG. 6.

In some cases, the graphical representation 700 may include a first segment 710 representative of sleep pattern data from the previous night's sleep and a second segment 715 representative of the determined circadian rhythm chronotype. The first segment 710 may include the wake that time that the user woke up for the current day, the bedtime that the user went to sleep the previous night, the midpoint 720-*a* of the user's sleep from the previous night, the sleep duration of the previous night, or a combination thereof. For example, the graphical representation 700 may indicate that the user, for the previous night, went to sleep at 10:00 PM and woke up at 6:00 AM. The midpoint 720-*a* may indicate that the midpoint of the user's sleep was 2:15 AM. The first side may indicate the time that the user goes to sleep, and the second side may indicate the time that the user wakes up.

In such cases, the system may cause the GUI 275 of the user device to display a first segment 710 of the circular representation 705 of the twenty-four hour timespan that includes the sleep pattern data from the previous night. In some examples, the first segment 710 may include an arch-shaped segment that represents the sleep pattern data from the previous night. For example, the sleep pattern data from the previous night may be included in an outermost circular line with a first color. The first segment 710 may include a midpoint 720-*a* that is representative of the user's midpoint of sleep from the previous night. In such cases, the midpoint 720-*a* of the first segment 710 may allow the user to quickly and effectively identify a time of night that user's midpoint of sleep occurs. The time of the midpoint 720-*a* may indicate whether the user is a morning person or an evening person.

In some cases, the graphical representation 700 may include a second segment 715 representative of an averaging of the sleep pattern data of the first set of physiological data over the period of time. The second segment 715 may include an average wake time that the user wakes up, an average bedtime that the user goes to sleep, an average sleep midpoint 720-*b* time, an average sleep duration, or a combination thereof. For example, the graphical representation 700 may indicate that the user, on average, goes to sleep at 11:00 PM and wakes up at 7:00 AM. The midpoint 720-*b* may indicate that the average midpoint of the user's sleep is 2:45 AM. The first side may indicate the average time that the user goes to sleep, and the second side may indicate the average time that the user wakes up.

In such cases, the system may cause the GUI 275 of the user device to display the second segment 715 of the circular representation 705 of the twenty-four hour timespan that includes the averaging of the sleep pattern data of the first set of physiological data over the period of time. In some examples, the second segment 715 may include an arch-shaped segment that represents the averaging of the sleep pattern data of the first set of physiological data over the period of time. For example, the average sleep pattern data may be included in an innermost circular line with a second color different than the first color. The second segment 715 may include a midpoint 720-*b* that is representative of the user's average midpoint of sleep. In such cases, the second segment 715 may allow the user to quickly and effectively to compare the sleep pattern data from the previous night to the determined circadian rhythm chronotype for the user. In such cases, first segment 710 may be easily compared to the second segment 715 to determine whether the user's previous night of sleep aligns with the determined circadian rhythm chronotype.

For example, the system may compare the determined circadian rhythm chronotype (e.g., second segment 715) and the received second set of physiological data (e.g., first segment 710). The system may compare the one or more features of the determined circadian rhythm chronotype and the received sleep data from the previous night's sleep. For example, the system may compare the sleep data associated with the determined circadian rhythm chronotype and the received sleep data from the previous night's sleep.

In such cases, the averaging of the sleep pattern data of the first set of physiological data over the period of time may be compared to the sleep pattern data collected over the previous sleep day. For example, the system may compare an average wake time that the user wakes up to a wake time from the previous night, an average bedtime that the user goes to sleep to a bedtime from the previous night, an average sleep duration to a sleep duration from the previous night, an average sleep midpoint to the sleep midpoint from the previous night, or a combination thereof.

In some examples, the graphical representation 700 may include one or more parameters. For example, the one or more parameters may be an example of an indication of the current time of day. In other examples, the one or more parameters may be an example of a message or an alert indicating heart rate data, an indication of a menstrual cycle, respiratory data, activity data, temperature data, or a combination thereof. In such cases, the system may cause the GUI 275 of the user device to display one or more parameters against the circular representation 705 of a twenty-four hour timespan. In some cases, the one or more parameters may overlay the graphical representation 700 against the circular representation 705 of a twenty-four hour timespan. In some cases, the graphical representation 700 may be an example of a generated report to display a picture of the user's body clock changes, seasonal variations, the effects of travel, lifestyle habits, or a combination thereof.

The graphical representation 700 may allow the user to visualize their long term habits on a twenty-four hour clock user interface component relative to the user's previous night of sleep. The graphical representation 700 may indicate a user's bedtime and wake-up times relative to their determined circadian rhythm chronotype. In such cases, the system may provide insights to the user on key variables that factor into determining the circadian profile (e.g., circadian rhythm chronotype) and providing recommendations (e.g., activity, sleep, and the like) for the current day given the comparison of the first segment 710 (e.g., sleep data from the previous night) with the second segment 715 (e.g., the determined circadian rhythm chronotype).

In some cases, the graphical representation 700 may include a static rendering. In such cases, the system may display to the user an interactive and helpful tool to give insight into the user's lifestyle. The patterns determined from the bio signals (e.g., physiological data) received may classify the user into a number of categories including, for example, but not limited to, morning people, evening people, highly active people, inactive people, or a combination thereof. In such cases, the graphical representation 700 may classify the users as users who are well-aligned with their circadian rhythm chronotype and users who are ill-aligned with their circadian rhythm chronotype.

Figure 8:
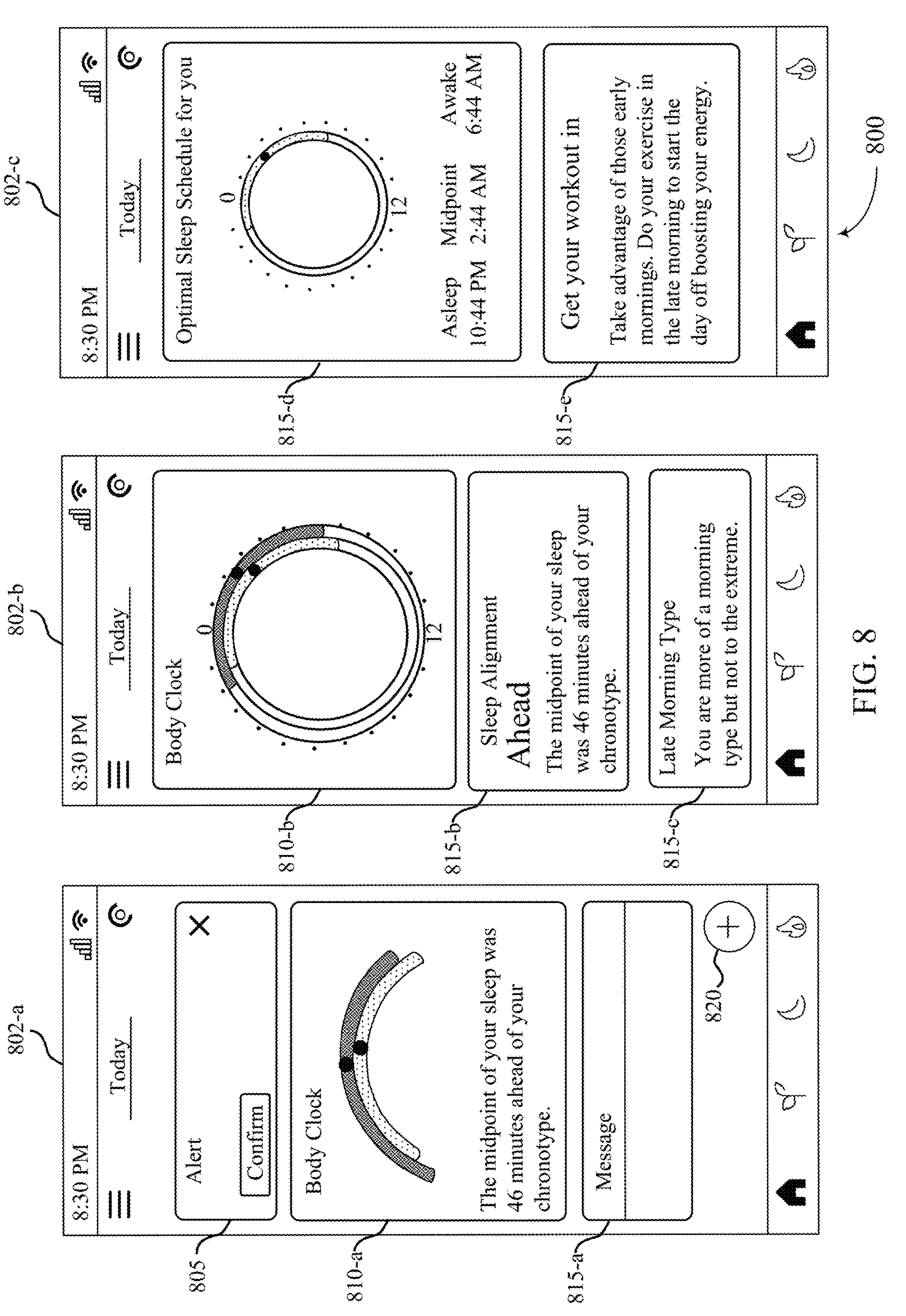
FIG. 8 shows an example of graphical user interfaces (GUIs) that supports techniques for determining a circadian rhythm chronotype in accordance with aspects of the present disclosure.

FIG. 8 shows an example of GUIs 800 that supports techniques for determining a circadian rhythm chronotype in accordance with aspects of the present disclosure. The GUI 800 may implement, or be implemented by, aspects of the system 100, system 200, system 300, timing diagrams 400, system 600, or any combination thereof. For example, the GUI 800 may be an example of a GUI 275 of a user device 106 (e.g., user device 106-*a*, 106-*b*, 106-*c*) corresponding to a user 102.

In some examples, the GUI 800 illustrates a series of application pages 802 that may be displayed to a user 102 via the GUI 800 (e.g., GUI 275 illustrated in FIG. 2). The system may generate a personalized tracking experience on the GUI 275 of the user device 106 to determine the circadian rhythm chronotype. Continuing with the examples above, after determining the circadian rhythm chronotype, the user 102 may be presented with the application page

802-*a* via GUI 800 upon opening the wearable application 250. The GUIs 800 may display an alert 805, graphical representations 810, messages 815, or a combination thereof. The graphical representations 810 may be an example of the graphical representation 500 described with reference to FIG. 5, graphical representation 700 described with reference to FIG. 7, a portion of graphical representation 500, a portion of graphical representation 700, or a combination thereof.

In some implementations, the user device and/or servers may generate alerts 805 associated with the determined circadian rhythm chronotype and/or circadian rhythm chronotype misalignment that may be displayed to the user via the GUI 800. In such cases, the application page 802-*a* may display an indication of the determined circadian rhythm chronotype via alert 805. For example, the application page 802-*a* may include the alert 805 on the home page.

In cases where a user's determined circadian rhythm chronotype is misaligned with the received physiological data, as described herein, the server may transmit an alert 805 to the user, where the alert 805 is associated with the misalignment. In particular, alerts 805 generated and displayed to the user via the GUI 800 may be associated with circadian rhythm chronotype misalignment and recommendations to return to the user's baseline determined circadian rhythm chronotype. In some cases, the alert 805 may display a recommendation of how to adjust their lifestyle on the day of the determined misalignment and/or in the days after the determined misalignment.

For example, the system may receive additional physiological data associated with the user from the wearable device subsequent to determining the circadian rhythm chronotype. The system may determine a misalignment between the received additional physiological data and the determined circadian rhythm chronotype in response to receiving the additional physiological data. In such cases, the system may determine deviations (e.g., a circadian misalignment) from the determined circadian rhythm chronotype.

In response to determining the misalignment between the received additional physiological data and the determined circadian rhythm, the user may receive an alert 805, that may indicate a message associated with the misalignment. For example, the alert 805 may indicate to the user when a user's physiological data deviates from the determined circadian rhythm chronotype. In such cases, the system may cause the GUI 800 of the user device to display an alert 805, messages 815, or both, associated with the misalignment. The alerts 805 may be configurable/customizable, such that the user may receive different alerts 805 based on the determined circadian rhythm chronotype, the misalignment, or both. In some cases, the alerts 805 may indicate the effect of the user's menstrual cycle on the determined circadian rhythm chronotype.

In some cases, the user may take remedial action to address the misalignment prior to the system displaying the alert 805. In such cases, the system may receive physiological data associated with the remedial action, and the system may refrain from displaying the alert 805 (e.g., override the alert 805). In some examples, the system may adjust the alert 805 based on receiving the physiological data associated with the remedial action.

Additionally, in some implementations, the application page 802-*a* may display one or more scores (e.g., Sleep score, Readiness Score, activity goal progress) for the user for the respective day. Moreover, in some cases, the misalignment may be used to update (e.g., modify) one or more scores associated with the user (e.g., Sleep score, Readiness Score). That is, data associated with the circadian rhythm chronotype misalignment may be used to update the scores for the user for the following calendar day after the misalignment was detected. In some cases, the Readiness Score may be updated based on the misalignment. In some cases, the messages 815-*a* displayed to the user via the GUI 800 of the user device may indicate how the misalignment affected the overall scores (e.g., overall Readiness Score) and/or the individual contributing factors. The system may be configured to dynamically update and compare the sleep regularity index. The GUI 800 may display the sleep regularity index for the viewed time period.

With reference to FIG. 5, the application page 802-*a* may display the graphical representations 810. For example, the system may cause the GUI 800 of the user device to display a graphical representation 810 of an averaging over the period of time of at least the continuous nighttime temperature data, the activity data, and the sleep pattern data. Based on patterns detected, the system may be able to provide additional context and insights regarding the graphical representation 810, thereby increasing the value to users by helping the users understand the graphical representation 810.

With reference to FIG. 7, the application pages 802-*a* and 802-*b* may display the graphical representations 810-*a* and 810-*b*, respectively. For example, the system may cause the GUI 800 of the user device to display the graphical representation 810-*a* of the user's sleep pattern data for the previous night's sleep compared to the determined circadian rhythm chronotype. The graphical representation 810-*a* may also include text that indicates how the midpoint of the user's sleep aligns with the determined circadian rhythm chronotype, as described herein. The graphical representation 810-*a* may be an example of a portion of the graphical representation 810-*b*.

In some cases, the graphical representations 810 may be shared socially by using user interface tools for social sharing. The graphical representations 810 may provide the user with a cross-section of the moment with respect to each individual component of the graphical representations 810. For example, the message 815-*a* may indicate that "You are highly active, awake" or "You are sleeping, temperature heading down" with respect to the graphical representations 810. In such cases, the user may compare the long-term patterns with today, yesterday, or last week's patterns. In some cases, the graphical representations 810 may include dynamic components such that the different segments may become animated and/or highlighted as the user moves from one segment to a different segment.

The GUI 800 may also include messages 815 that includes insights, recommendations, and the like associated with the determined circadian rhythm chronotype. The server of system may cause the GUI 800 of the user device to display messages 815 associated with the determined circadian rhythm chronotype. The user device 106 may display recommendations and/or information associated with the determined circadian rhythm chronotype via messages 815. As noted previously herein, an accurately determined circadian rhythm chronotype may be beneficial to a user's overall health by providing metrics to the user that may enable the user to understand how behavior changes (e.g., improvements in sleep, exercise, diet, and mood) may help increase the user's overall health and reduce an occurrence of circadian rhythm chronotype misalignment.

The system may cause the GUI 800 of the user device 106 to display the message 815-*a* associated with the comparison of the determined circadian rhythm chronotype and the received second set of physiological data (e.g., the sleep pattern data from the previous night), the determined circadian rhythm chronotype, the received second set of physiological data, or a combination thereof. For example, the graphical representation 810-*a* may indicate an averaging of the sleep pattern data of the first set of physiological data over the period of time (e.g., that is used to determine the circadian rhythm chronotype), the sleep pattern data from the previous night, an average wake time that the user wakes up, an average bedtime that the user goes to sleep, an average sleep midpoint time, an average sleep duration, or a combination thereof.

Continuing with the examples above, after selecting the graphical representation 810, the user 102 may be presented with the application page 802-*b* via GUI 800. As shown in FIG. 8, the application page 802-*b* may display a message 815-*c* associated with the determined circadian rhythm chronotype. In such cases, the system may cause the GUI 800 of the user device to display messages 815 that may provide recommendations to the user based on the determined circadian rhythm chronotype.

Application page 802-*b* may display a message 815-*c* that may indicate "You're physically active in the morning. You go to bed relatively early, and you wake up early. Your sleep temperature reaches its minimum at almost 3 o'clock" or "You are a highly active, morning type!" In some cases, the messages 815-*c* may indicate "You are a night wolf" or "You're an early bird." In other examples, the messages 815-*c* may indicate "You are a late morning type. You are more of a morning type but not that extreme." In such cases, the message 815-*c* may provide insight for the user regarding morning type individuals. For example, the message 815-*c* may indicate "Morning types with early bedtimes have a lower risk for cardiovascular disease, less obesity, and may have lower risks for mental health disorders, including depression, anxiety, and others."

In some cases, the messages 815-*b* may indicate how well each night of sleep aligns with the user's recommended bedtime and wake time (e.g., with respect to the sleep pattern data). For example, the message 815-*b* may indicate the user's sleep alignment and whether the user's previous night of sleep is aligned with the determined circadian rhythm chronotype. In such cases, the message 815-*b* may indicate that the user's current sleep pattern data (e.g., sleep data from the previous night) is ahead, behind, or aligns with the determined circadian rhythm chronotype. For example, the message 815-*b* may indicate "The midpoint of your sleep was 46 minutes ahead of your chronotype."

In some examples, the message 815-*b* may indicate "You are within 85% of your recommended pattern. Keep up the good work!" In some cases, the graphical representation 810 may be configured to focus on individual aspects by filtering out or dimming other parts of the graphical representation 810 and receiving specific insights on the focused aspect. For example, the user may highlight (e.g., select) the activity data of the graphical representation 810, and the message 815 may indicate "Activity pattern shows you have regular activity in the morning hours, corresponding nicely with your recommended activity window."

In cases where the system may detect a circadian rhythm chronotype misalignment, the messages 815-*b* may provide suggestions for the user in order to improve their general health. For example, the message may indicate "If you feel really low on energy, why not try switching to rest mode for today," or "Since you went to bed later than usual, devote today for rest." In such cases, accurately determining the circadian rhythm chronotype and detecting misalignments may increase the accuracy and efficiency of the Readiness Score and activity scores.

The message 815-*b* may include a timetable or calendar view to enable to the user to adjust the timespan and explore the body clock. For example, the message 815-*b* may include a toggle to allow the user to select a duration of time to show the averaging on the graphical representation 810-*b*. For example, the message may include a toggle to select a quantity of months (e.g., March to June), a quantity of weekdays (e.g., Saturday and Sundays only, Monday through Sunday, etc.), a quantity of weeks (e.g., 2 weeks), or a combination thereof.

After selecting the message 815-*c*, the user 102 may be presented with application page 802-*c* via GUI 800. For example, the message 815-*d* and message 815-*e* may include a recommended time of day that the user is active, a recommended wake time that the user wakes up, a recommended bedtime that the user goes to sleep, a recommended sleep duration, a recommended time of day that the user rests, or a combination thereof.

In some cases, the message 815-*e* may indicate "Feeling drowsy? Your body is going through a low energy afternoon dip. Don't worry if you feel lazy; there's an energy peak coming in an hour." In such cases, the message 815-*e* may further provide an insight regarding recommended times to exercise, to focus, and the like. For example, the application page 802-*c* may display the message 815-*e* that may indicate "The optimal time for a workout is 2:30 PM-5:00 PM for greatest cardiovascular efficiency and muscle strength." In other examples, the message 815-*e* may indicate "Take advantage of those early mornings. Do your exercise in the late morning to start the day off boosting your energy." In some cases, the message 815-3 may indicate "Take advantage of the mid-afternoon to focus on the task at hand. Do your work in the mid-afternoon to complete your tasks efficiently and effectively." Personalized insights may indicate aspects of collected physiological data (e.g., contributing factors within the physiological data) that were used to determine the circadian rhythm chronotype. In some cases, the messages 815 may provide personalized insights regarding the graphical representations 810.

The application page 802-*c* may display a message 815-*d* that indicates an optical sleep schedule for the user. In some cases, the message 815-*d* may include a recommended schedule for the user including bedtimes, wake times, exercise times, focused times, rest times, or a combination thereof. For example, the message 815-*d* may indicate "6:00 AM-6:30 AM: The sharpest rise in blood pressure, the optimal wake-up time. 6:00 AM-12:00 AM: High alertness, focus on deep or creative work. 1:30 PM-2:00 PM: Afternoon dip. Period of low energy. Take it easy during this time." The message 815-*d* may indicate a recommended bedtime, wake time, a sleep midpoint, or a combination thereof. In such cases, the message 815 may recommend a bedtime and/or a wake time based on the determined circadian rhythm chronotype.

In some cases, the messages 815 may indicate how the information gathered from the user's circadian portrait may be leveraged in travel mode in order to assist the users to adjust their body clock from jet lag and recover to the new time zone. For example, the messages 815 may indicate a melatonin onset estimation, alertness timeline estimation, exercise timeline recommendation, more personalized bedtime recommendation, light therapy assist, or a combination thereof associated with jet lag.

For example, the determined circadian rhythm chronotype may be used to suggest bedtimes in the new time zone based on the user's determined circadian rhythm chronotype, a time of the nighttime temperature minimum derived from the historical data in the original time zone, the user's sleep history stats, or a combination thereof. In such cases, the message 815 may provide a recommendation to adjust/plan the user's sleep-wake schedule for the first number of days in a new time zone.

In some cases, the user may log symptoms or moments via user input 820. For example, the system may receive user input (e.g., tags) to log symptoms associated with a relaxed state (e.g., that the user experiences a Moment). In some examples, the system may identify a restorative moment that the user is in a relaxed state. In such cases, the system may determine the circadian rhythm chronotype based on identifying the restorative moment. For example, the system may use the restorative time to determine the circadian rhythm chronotype.

In some implementations, the system may be configured to receive user inputs 820 regarding determined circadian rhythm chronotype in order to train classifiers (e.g., supervised learning for a machine learning classifier) and improve circadian rhythm chronotype determination techniques. For example, the user device may display a determination of the circadian rhythm chronotype. Subsequently, the user may input one or more user inputs, such as an onset of symptoms, a confirmation of the determined circadian rhythm chronotype, and the like. These user inputs 820 may then be input into the classifier to train the classifier. In other words, the user inputs 820 may be used to validate, or confirm, the determined circadian rhythm chronotype.

Figure 9:
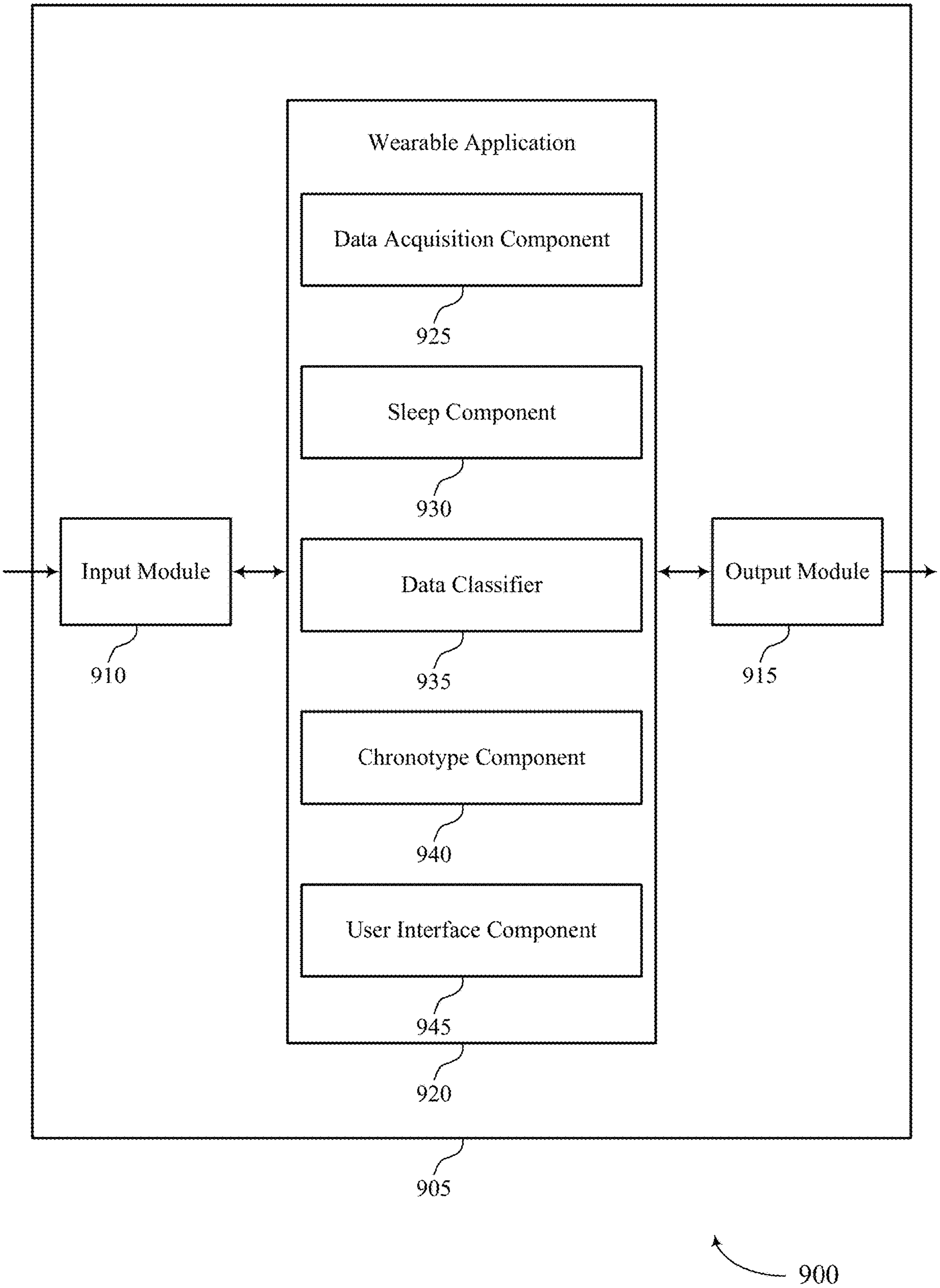
FIG. 9 shows a block diagram of an apparatus that supports techniques for determining a circadian rhythm chronotype in accordance with aspects of the present disclosure.

FIG. 9 shows a block diagram 900 of a device 905 that supports techniques for determining a circadian rhythm chronotype in accordance with aspects of the present disclosure. The device 905 may include an input module 910, an output module 915, and a wearable application 920. The device 905 may also include a processor. Each of these components may be in communication with one another (e.g., via one or more buses).

The input module 910 may provide a means for receiving information such as packets, user data, control information, or any combination thereof associated with various information channels (e.g., control channels, data channels, information channels related to illness detection techniques). Information may be passed on to other components of the device 905. The input module 910 may utilize a single antenna or a set of multiple antennas.

The output module 915 may provide a means for transmitting signals generated by other components of the device 905. For example, the output module 915 may transmit information such as packets, user data, control information, or any combination thereof associated with various information channels (e.g., control channels, data channels, information channels related to illness detection techniques). In some examples, the output module 915 may be co-located with the input module 910 in a transceiver module. The output module 915 may utilize a single antenna or a set of multiple antennas.

For example, the wearable application 920 may include a data acquisition component 925, a sleep component 930, a data classifier 935, a chronotype component 940, a user interface component 945, or any combination thereof. In some examples, the wearable application 920, or various components thereof, may be configured to perform various operations (e.g., receiving, monitoring, transmitting) using or otherwise in cooperation with the input module 910, the output module 915, or both. For example, the wearable application 920 may receive information from the input module 910, send information to the output module 915, or be integrated in combination with the input module 910, the output module 915, or both to receive information, transmit information, or perform various other operations as described herein.

The wearable application 920 may support determining a circadian rhythm chronotype on an application running on an operating system of user device and associated with a wearable device in accordance with examples as disclosed herein. The data acquisition component 925 may be configured as or otherwise support a means for receiving, from the wearable device, a first set of physiological data measured from a user by the wearable device collected over a period of time, the first set of physiological data comprising at least nighttime temperature data, activity data, and sleep pattern data. The sleep component 930 may be configured as or otherwise support a means for receiving, from the wearable device, a second set of physiological data measured from the user by the wearable device collected over a previous sleep day, the second set of physiological data comprising at least sleep pattern data. The data classifier 935 may be configured as or otherwise support a means for classifying, using a machine learning model, the first set of physiological data into the circadian rhythm chronotype based at least in part on inputting the first set of physiological data into the machine learning model. The chronotype component 940 may be configured as or otherwise support a means for comparing, by the application that is configured for processing data received from the wearable device, the determined circadian rhythm chronotype and the received second set of physiological data. The user interface component 945 may be configured as or otherwise support a means for causing a graphical user interface of the user device to display a message associated with the comparison, the determined circadian rhythm chronotype, the received second set of physiological data, or a combination thereof.

Figure 10:
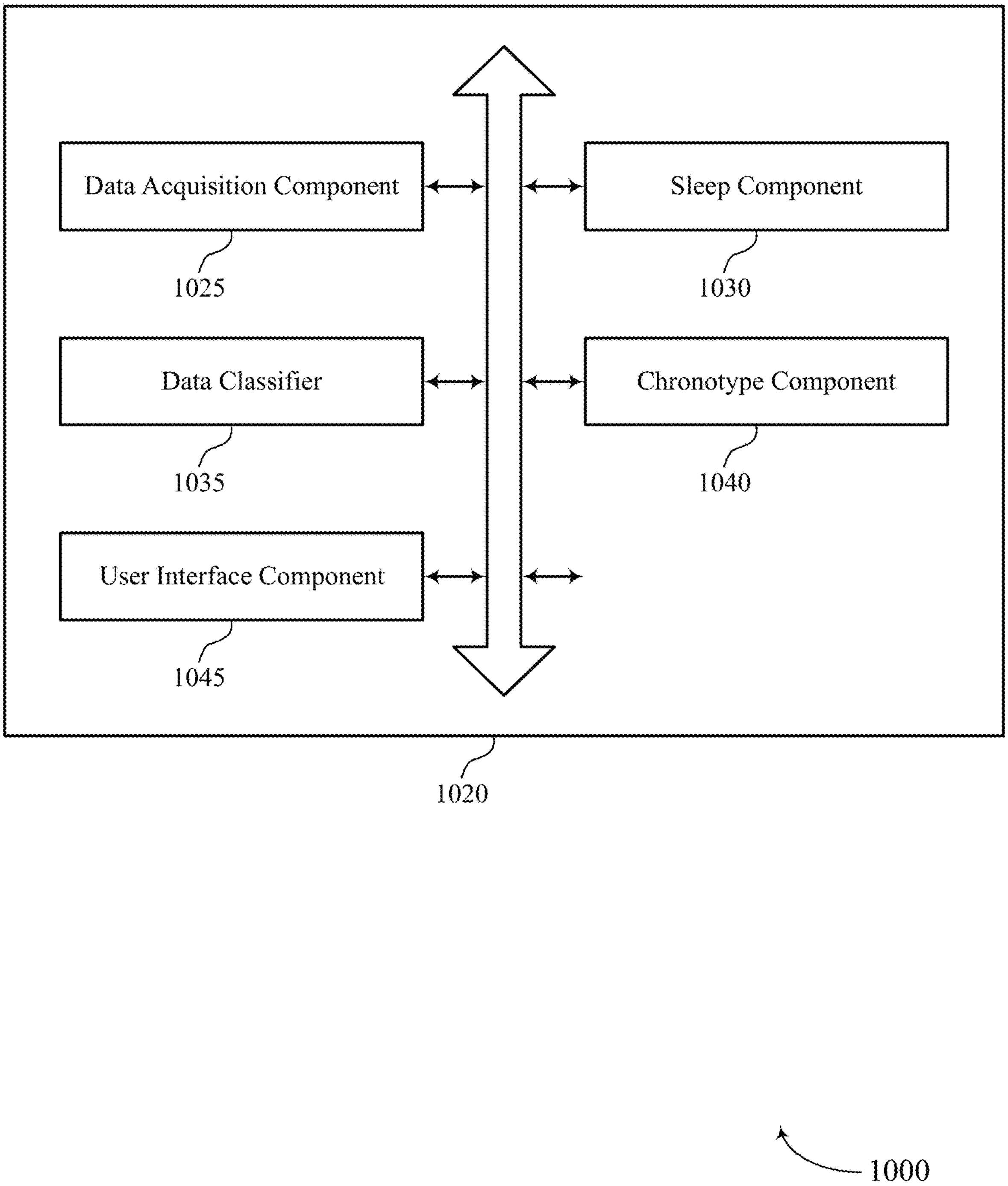
FIG. 10 shows a block diagram of a wearable application that supports techniques for determining a circadian rhythm chronotype in accordance with aspects of the present disclosure.

FIG. 10 shows a block diagram 1000 of a wearable application 1020 that supports techniques for determining a circadian rhythm chronotype in accordance with aspects of the present disclosure. The wearable application 1020 may be an example of aspects of a wearable application or a wearable application 920, or both, as described herein. The wearable application 1020, or various components thereof, may be an example of means for performing various aspects of techniques for determining a circadian rhythm chronotype as described herein. For example, the wearable application 1020 may include a data acquisition component 1025, a sleep component 1030, a data classifier 1035, a chronotype component 1040, a user interface component 1045, or any combination thereof. Each of these components may communicate, directly or indirectly, with one another (e.g., via one or more buses).

The wearable application 1020 may support determining a circadian rhythm chronotype on an application running on an operating system of user device and associated with a wearable device in accordance with examples as disclosed herein. The data acquisition component 1025 may be configured as or otherwise support a means for receiving, from the wearable device, a first set of physiological data measured from a user by the wearable device collected over a period of time, the first set of physiological data comprising at least nighttime temperature data, activity data, and sleep pattern data. The sleep component 1030 may be configured as or otherwise support a means for receiving, from the wearable device, a second set of physiological data measured from the user by the wearable device collected over a previous sleep day, the second set of physiological data comprising at least sleep pattern data. The data classifier 1035 may be configured as or otherwise support a means for classifying, using a machine learning model, the first set of physiological data into the circadian rhythm chronotype based at least in part on inputting the first set of physiological data into the machine learning model. The chronotype component 1040 may be configured as or otherwise support a means for comparing, by the application that is configured for processing data received from the wearable device, the determined circadian rhythm chronotype and the received second set of physiological data. The user interface component 1045 may be configured as or otherwise support a means for causing a graphical user interface of the user device to display a message associated with the comparison, the determined circadian rhythm chronotype, the received second set of physiological data, or a combination thereof.

In some examples, the user interface component 1045 may be configured as or otherwise support a means for causing the graphical user interface of the user device to display a graphical representation of an averaging of the sleep pattern data of the first set of physiological data over the period of time.

In some examples, the averaging of the sleep pattern data comprises an average wake time that the user wakes up, an average bedtime that the user goes to sleep, an average sleep midpoint time, an average sleep duration, or a combination thereof.

In some examples, the user interface component 1045 may be configured as or otherwise support a means for overlaying the graphical representation of the averaging of the sleep pattern data of the first set of physiological data over the period of time against a representation of a twenty-four hour timespan.

In some examples, the user interface component 1045 may be configured as or otherwise support a means for causing the graphical user interface of the user device to display a segment of the representation of the twenty-four hour timespan that comprises the averaging of the sleep pattern data of the first set of physiological data over the period of time.

In some examples, the segment represents the averaging of the sleep pattern data of the first set of physiological data over the period of time as a shaped portion having a first side indicating an average time the user goes to sleep, a second side indicating an average time the user wakes up, and a midpoint that is positioned between the first side and the second side and indicates an average time of a sleep midpoint of the user.

In some examples, the data acquisition component 1025 may be configured as or otherwise support a means for identifying a time of night associated with a nighttime temperature minimum based at least in part on receiving the first set of physiological data, wherein classifying the first set of physiological data into the circadian rhythm chronotype is based at least in part on identifying the time of night associated with the nighttime temperature minimum.

In some examples, the data classifier 1035 may be configured as or otherwise support a means for processing, by the application, the sleep pattern data of the first set of physiological data to extract at least a standard deviation of a sleep midpoint, a median wake time wake that the user wakes up, a median bedtime that the user goes to sleep, or a combination thereof. In some examples, the data classifier 1035 may be configured as or otherwise support a means for processing, by the application, the activity data of the first set of physiological data to extract at least an average metabolic equivalent of task (MET) value, a time that the user is active, or both. In some examples, the data classifier 1035 may be configured as or otherwise support a means for processing, by the application, the nighttime temperature data to extract at least an average skin temperature, an average skin temperature for a plurality of highest temperature values of a consecutive twenty-four hour timespan, an average skin temperature for a plurality of lowest temperature values of a consecutive twenty-four hour timespan, or a combination thereof. In some examples, classifying the first set of physiological data into the circadian rhythm chronotype is based at least in part processing, by the application, the sleep pattern data, the activity data, and the nighttime temperature data.

In some examples, the chronotype component 1040 may be configured as or otherwise support a means for determining a misalignment between the received second set of physiological data and the determined circadian rhythm chronotype based at least in part on comparing the determined circadian rhythm chronotype and the received second set of physiological data.

In some examples, the message comprises a recommended time of day that the user is active, a recommended wake time that the user wakes up, a recommended bedtime that the user goes to sleep, a recommended sleep duration, a recommended time of day that the user rests, a recommended time of day that the user is focused, a sleep alignment message, a sleep misalignment message, or a combination thereof.

In some examples, the nighttime temperature data comprises continuous nighttime temperature data.

In some examples, the wearable device comprises a wearable ring device.

In some examples, the wearable device collects the first set of physiological data and the second set of physiological data from the user based on arterial blood flow, capillary blood flow, arteriole blood flow, or a combination thereof.

Figure 11:
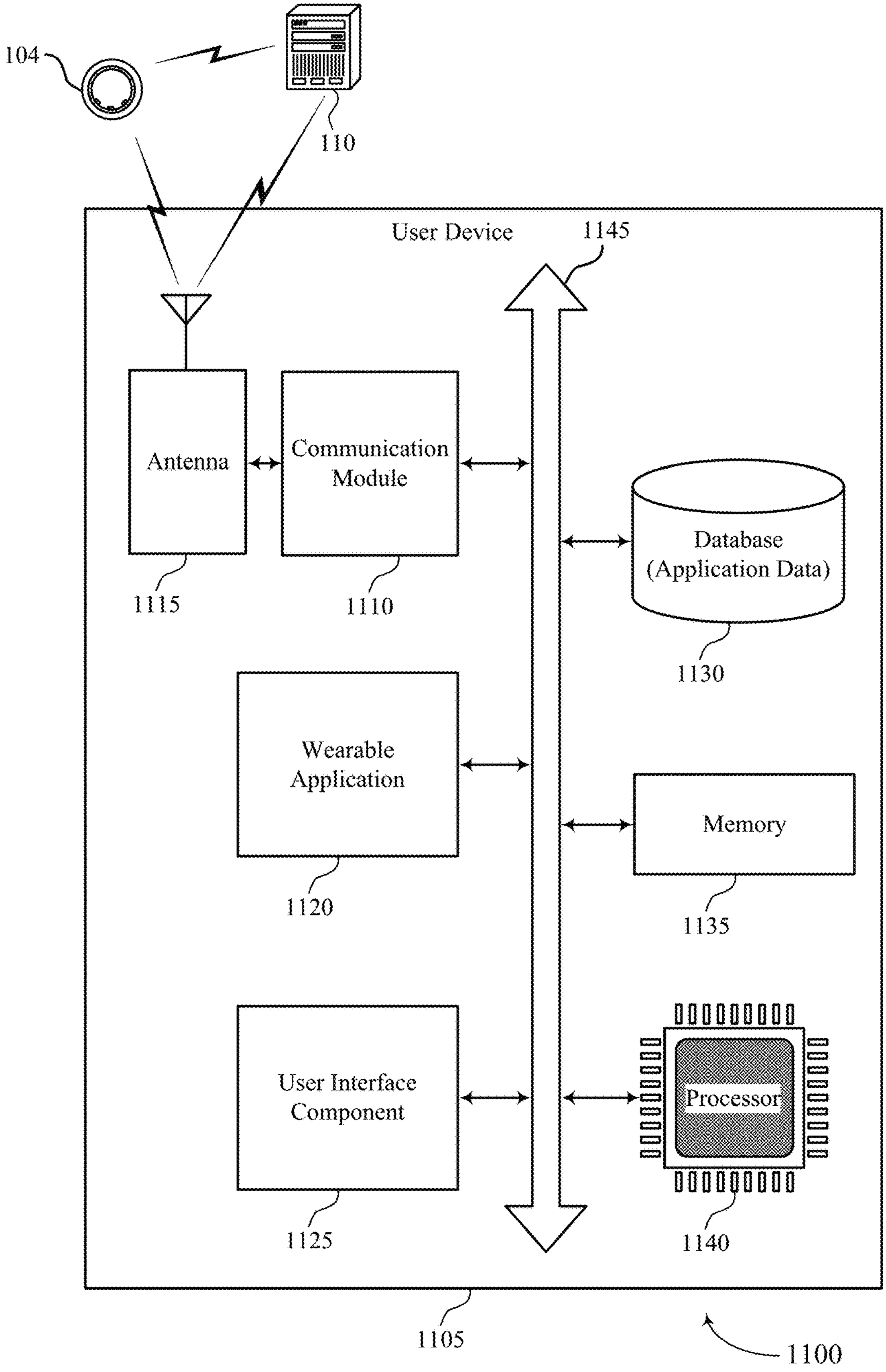
FIG. 11 shows a diagram of a system including a device that supports techniques for determining a circadian rhythm chronotype in accordance with aspects of the present disclosure.

FIG. 11 shows a diagram of a system 1100 including a device 1105 that supports techniques for determining a circadian rhythm chronotype in accordance with aspects of the present disclosure. The device 1105 may be an example of or include the components of a device 905 as described herein. The device 1105 may include an example of a user device 106, as described previously herein. The device 1105 may include components for bi-directional communications including components for transmitting and receiving communications with a wearable device 104 and a server 110, such as a wearable application 1120, a communication module 1110, an antenna 1115, a user interface component 1125, a database (application data) 1130, a memory 1135, and a processor 1140. These components may be in electronic communication or otherwise coupled (e.g., operatively, communicatively, functionally, electronically, electrically) via one or more buses (e.g., a bus 1145).

The communication module 1110 may manage input and output signals for the device 1105 via the antenna 1115. The communication module 1110 may include an example of the communication module 220-*b* of the user device 106 shown and described in FIG. 2. In this regard, the communication module 1110 may manage communications with the ring 104 and the server 110, as illustrated in FIG. 2. The communication module 1110 may also manage peripherals not integrated into the device 1105. In some cases, the communication module 1110 may represent a physical connection or port to an external peripheral. In some cases, the communication module 1110 may utilize an operating system such as iOS®, ANDROID®, MS-DOS®, MS-WINDOWS®, OS/2®, UNIX®, LINUX®, or another known operating system. In other cases, the communication module 1110 may represent or interact with a wearable device (e.g., ring 104), modem, a keyboard, a mouse, a touchscreen, or a similar device. In some cases, the communication module 1110 may be implemented as part of the processor 1140. In some examples, a user may interact with the device 1105 via the communication module 1110, user interface component 1125, or via hardware components controlled by the communication module 1110.

In some cases, the device 1105 may include a single antenna 1115. However, in some other cases, the device 1105 may have more than one antenna 1115, that may be capable of concurrently transmitting or receiving multiple wireless transmissions. The communication module 1110 may communicate bi-directionally, via the one or more antennas 1115, wired, or wireless links as described herein. For example, the communication module 1110 may represent a wireless transceiver and may communicate bi-directionally with another wireless transceiver. The communication module 1110 may also include a modem to modulate the packets, to provide the modulated packets to one or more antennas 1115 for transmission, and to demodulate packets received from the one or more antennas 1115.

The user interface component 1125 may manage data storage and processing in a database 1130. In some cases, a user may interact with the user interface component 1125. In other cases, the user interface component 1125 may operate automatically without user interaction. The database 1130 may be an example of a single database, a distributed database, multiple distributed databases, a data store, a data lake, or an emergency backup database.

The memory 1135 may include RAM and ROM. The memory 1135 may store computer-readable, computer-executable software including instructions that, when executed, cause the processor 1140 to perform various functions described herein. In some cases, the memory 1135 may contain, among other things, a BIOS that may control basic hardware or software operation such as the interaction with peripheral components or devices.

The processor 1140 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 1140 may be configured to operate a memory array using a memory controller. In other cases, a memory controller may be integrated into the processor 1140. The processor 1140 may be configured to execute computer-readable instructions stored in a memory 1135 to perform various functions (e.g., functions or tasks supporting a method and system for sleep staging algorithms).

The wearable application 1120 may support determining a circadian rhythm chronotype on an application running on an operating system of user device and associated with a wearable device in accordance with examples as disclosed herein. For example, the wearable application 1120 may be configured as or otherwise support a means for receiving, from the wearable device, a first set of physiological data measured from a user by the wearable device collected over a period of time, the first set of physiological data comprising at least nighttime temperature data, activity data, and sleep pattern data. The wearable application 1120 may be configured as or otherwise support a means for receiving, from the wearable device, a second set of physiological data measured from the user by the wearable device collected over a previous sleep day, the second set of physiological data comprising at least sleep pattern data. The wearable application 1120 may be configured as or otherwise support a means for classifying, using a machine learning model, the first set of physiological data into the circadian rhythm chronotype based at least in part on inputting the first set of physiological data into the machine learning model. The wearable application 1120 may be configured as or otherwise support a means for comparing, by the application that is configured for processing data received from the wearable device, the determined circadian rhythm chronotype and the received second set of physiological data. The wearable application 1120 may be configured as or otherwise support a means for causing a graphical user interface of the user device to display a message associated with the comparison, the determined circadian rhythm chronotype, the received second set of physiological data, or a combination thereof.

By including or configuring the wearable application 1120 in accordance with examples as described herein, the device 1105 may support techniques for improved communication reliability, reduced latency, improved user experience related to reduced processing, reduced power consumption, more efficient utilization of communication resources, improved coordination between devices, longer battery life, improved utilization of processing capability, and the like.

The wearable application 1120 may include an application (e.g., "app"), program, software, or other component that is configured to facilitate communications with a ring 104, server 110, other user devices 106, and the like. For example, the wearable application 1120 may include an application executable on a user device 106 that is configured to receive data (e.g., physiological data) from a ring 104, perform processing operations on the received data, transmit and receive data with the servers 110, and cause presentation of data to a user 102.

Figure 12:
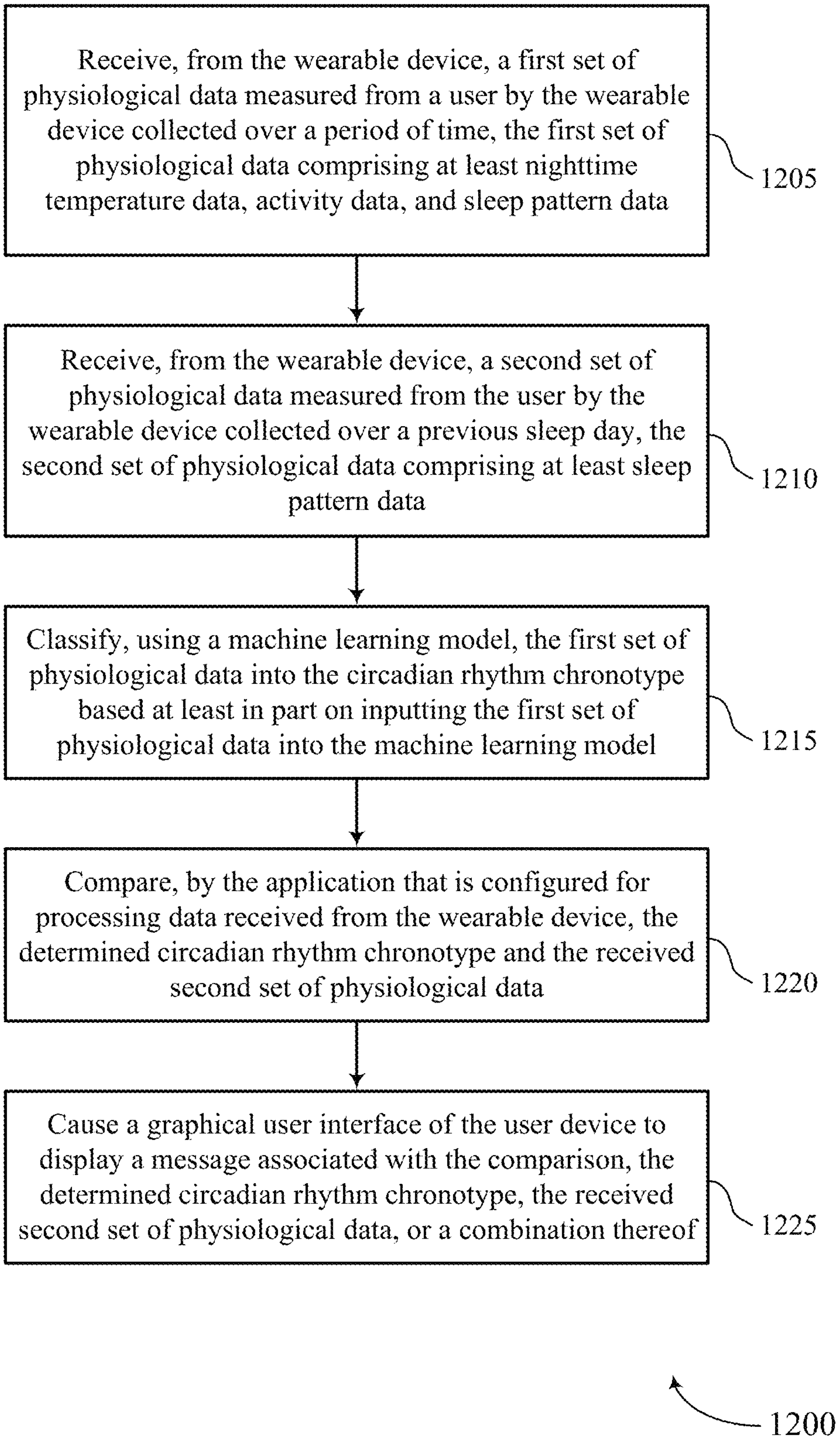
FIGS. 12 and 13 show flowcharts illustrating methods that support techniques for determining a circadian rhythm chronotype in accordance with aspects of the present disclosure.

FIG. 12 shows a flowchart illustrating a method 1200 that supports techniques for determining a circadian rhythm chronotype in accordance with aspects of the present disclosure. The operations of the method 1200 may be implemented by a user device or its components as described herein. For example, the operations of the method 1200 may be performed by a user device as described with reference to FIGS. 1 through 11. In some examples, a user device may execute a set of instructions to control the functional elements of the user device to perform the described functions. Additionally, or alternatively, the user device may perform aspects of the described functions using special-purpose hardware.

At 1205, the method may include receiving, from the wearable device, a first set of physiological data measured from a user by the wearable device collected over a period of time, the first set of physiological data comprising at least nighttime temperature data, activity data, and sleep pattern data. The operations of block 1205 may be performed in accordance with examples as disclosed herein. In some examples, aspects of the operations of 1205 may be performed by a data acquisition component 1025 as described with reference to FIG. 10.

At 1210, the method may include receiving, from the wearable device, a second set of physiological data measured from the user by the wearable device collected over a previous sleep day, the second set of physiological data comprising at least sleep pattern data. The operations of block 1210 may be performed in accordance with examples as disclosed herein. In some examples, aspects of the operations of 1210 may be performed by a sleep component 1030 as described with reference to FIG. 10.

At 1215, the method may include classifying, using a machine learning model, the first set of physiological data into the circadian rhythm chronotype based at least in part on inputting the first set of physiological data into the machine learning model. The operations of block 1215 may be performed in accordance with examples as disclosed herein. In some examples, aspects of the operations of 1215 may be performed by a data classifier 1035 as described with reference to FIG. 10.

At 1220, the method may include comparing, by the application that is configured for processing data received from the wearable device, the determined circadian rhythm chronotype and the received second set of physiological data. The operations of block 1220 may be performed in accordance with examples as disclosed herein. In some examples, aspects of the operations of 1220 may be performed by a chronotype component 1040 as described with reference to FIG. 10.

At 1225, the method may include causing a graphical user interface of the user device to display a message associated with the comparison, the determined circadian rhythm chronotype, the received second set of physiological data, or a combination thereof. The operations of block 1225 may be performed in accordance with examples as disclosed herein. In some examples, aspects of the operations of 1225 may be performed by a user interface component 1045 as described with reference to FIG. 10.

Figure 13:
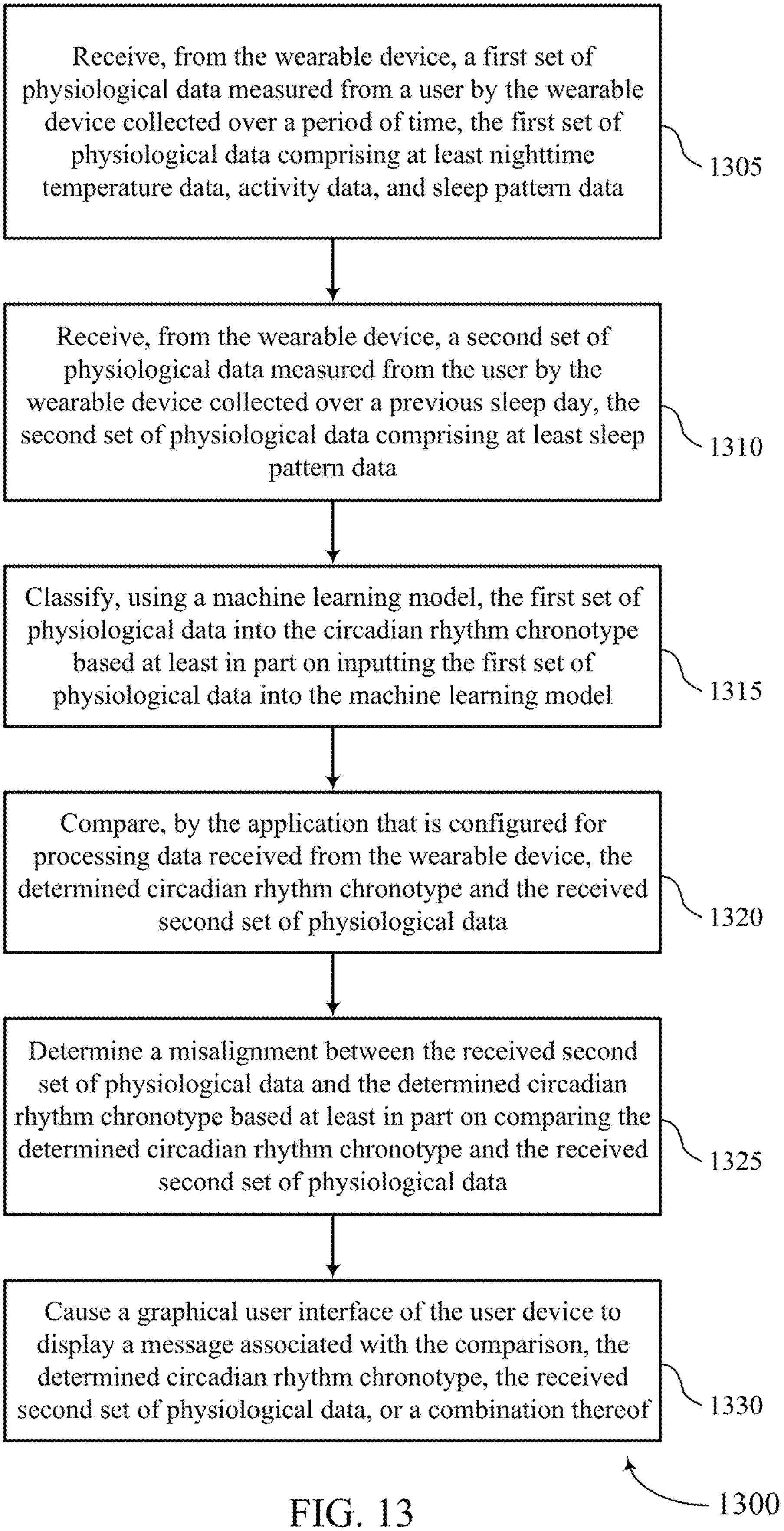

FIG. 13 shows a flowchart illustrating a method 1300 that supports techniques for determining a circadian rhythm chronotype in accordance with aspects of the present disclosure. The operations of the method 1300 may be implemented by a user device or its components as described herein. For example, the operations of the method 1300 may be performed by a user device as described with reference to FIGS. 1 through 11. In some examples, a user device may execute a set of instructions to control the functional elements of the user device to perform the described functions. Additionally, or alternatively, the user device may perform aspects of the described functions using special-purpose hardware.

At 1305, the method may include receiving, from the wearable device, a first set of physiological data measured from a user by the wearable device collected over a period of time, the first set of physiological data comprising at least nighttime temperature data, activity data, and sleep pattern data. The operations of block 1305 may be performed in accordance with examples as disclosed herein. In some examples, aspects of the operations of 1305 may be performed by a data acquisition component 1025 as described with reference to FIG. 10.

At 1310, the method may include receiving, from the wearable device, a second set of physiological data measured from the user by the wearable device collected over a previous sleep day, the second set of physiological data comprising at least sleep pattern data. The operations of block 1310 may be performed in accordance with examples as disclosed herein. In some examples, aspects of the operations of 1310 may be performed by a sleep component 1030 as described with reference to FIG. 10.

At 1315, the method may include classifying, using a machine learning model, the first set of physiological data into the circadian rhythm chronotype based at least in part on inputting the first set of physiological data into the machine learning model. The operations of block 1315 may be performed in accordance with examples as disclosed herein. In some examples, aspects of the operations of 1315 may be performed by a data classifier 1035 as described with reference to FIG. 10.

At 1320, the method may include comparing, by the application that is configured for processing data received from the wearable device, the determined circadian rhythm chronotype and the received second set of physiological data. The operations of block 1320 may be performed in accordance with examples as disclosed herein. In some examples, aspects of the operations of 1320 may be performed by a chronotype component 1040 as described with reference to FIG. 10.

At 1325, the method may include determining a misalignment between the received second set of physiological data and the determined circadian rhythm chronotype based at least in part on comparing the determined circadian rhythm chronotype and the received second set of physiological data. The operations of block 1325 may be performed in accordance with examples as disclosed herein. In some examples, aspects of the operations of 1325 may be performed by a chronotype component 1040 as described with reference to FIG. 10.

At 1330, the method may include causing a graphical user interface of the user device to display a message associated with the comparison, the determined circadian rhythm chronotype, the received second set of physiological data, or a combination thereof. The operations of block 1330 may be performed in accordance with examples as disclosed herein. In some examples, aspects of the operations of 1330 may be performed by a user interface component 1045 as described with reference to FIG. 10.

It should be noted that the methods described above describe possible implementations, and that the operations and the steps may be rearranged or otherwise modified and that other implementations are possible. Furthermore, aspects from two or more of the methods may be combined.

A method for determining a circadian rhythm chronotype on an application running on an operating system of user device and associated with a wearable device is described. The method may include receiving, from the wearable device, a first set of physiological data measured from a user by the wearable device collected over a period of time, the first set of physiological data comprising at least nighttime temperature data, activity data, and sleep pattern data, receiving, from the wearable device, a second set of physiological data measured from the user by the wearable device collected over a previous sleep day, the second set of physiological data comprising at least sleep pattern data, classifying, using a machine learning model, the first set of physiological data into the circadian rhythm chronotype based at least in part on inputting the first set of physiological data into the machine learning model, comparing, by the application that is configured for processing data received from the wearable device, the determined circadian rhythm chronotype and the received second set of physiological data, and causing a graphical user interface of the user device to display a message associated with the comparison, the determined circadian rhythm chronotype, the received second set of physiological data, or a combination thereof.

An apparatus for determining a circadian rhythm chronotype on an application running on an operating system of user device and associated with a wearable device is described. The apparatus may include a processor, memory coupled with the processor, and instructions stored in the memory. The instructions may be executable by the processor to cause the apparatus to receive, from the wearable device, a first set of physiological data measured from a user by the wearable device collected over a period of time, the first set of physiological data comprising at least nighttime temperature data, activity data, and sleep pattern data, receive, from the wearable device, a second set of physiological data measured from the user by the wearable device collected over a previous sleep day, the second set of physiological data comprising at least sleep pattern data, classify, using a machine learning model, the first set of physiological data into the circadian rhythm chronotype based at least in part on inputting the first set of physiological data into the machine learning model, compare, by the application that is configured for processing data received from the wearable device, the determined circadian rhythm chronotype and the received second set of physiological data, and cause a graphical user interface of the user device to display a message associated with the comparison, the determined circadian rhythm chronotype, the received second set of physiological data, or a combination thereof.

Another apparatus for determining a circadian rhythm chronotype on an application running on an operating system of user device and associated with a wearable device is described. The apparatus may include means for receiving, from the wearable device, a first set of physiological data measured from a user by the wearable device collected over a period of time, the first set of physiological data comprising at least nighttime temperature data, activity data, and sleep pattern data, means for receiving, from the wearable device, a second set of physiological data measured from the user by the wearable device collected over a previous sleep day, the second set of physiological data comprising at least sleep pattern data, means for classifying, using a machine learning model, the first set of physiological data into the circadian rhythm chronotype based at least in part on inputting the first set of physiological data into the machine learning model, means for comparing, by the application that is configured for processing data received from the wearable device, the determined circadian rhythm chronotype and the received second set of physiological data, and means for causing a graphical user interface of the user device to display a message associated with the comparison, the determined circadian rhythm chronotype, the received second set of physiological data, or a combination thereof.

A non-transitory computer-readable medium storing code for determining a circadian rhythm chronotype on an application running on an operating system of user device and associated with a wearable device is described. The code may include instructions executable by a processor to receive, from the wearable device, a first set of physiological data measured from a user by the wearable device collected over a period of time, the first set of physiological data comprising at least nighttime temperature data, activity data, and sleep pattern data, receive, from the wearable device, a second set of physiological data measured from the user by the wearable device collected over a previous sleep day, the second set of physiological data comprising at least sleep pattern data, classify, using a machine learning model, the first set of physiological data into the circadian rhythm chronotype based at least in part on inputting the first set of physiological data into the machine learning model, compare, by the application that is configured for processing data received from the wearable device, the determined circadian rhythm chronotype and the received second set of physiological data, and cause a graphical user interface of the user device to display a message associated with the comparison, the determined circadian rhythm chronotype, the received second set of physiological data, or a combination thereof.

Some examples of the method, apparatuses, and non-transitory computer-readable medium described herein may further include operations, features, means, or instructions for causing the graphical user interface of the user device to display a graphical representation of an averaging of the sleep pattern data of the first set of physiological data over the period of time.

In some examples of the method, apparatuses, and non-transitory computer-readable medium described herein, the averaging of the sleep pattern data comprises an average wake time that the user wakes up, an average bedtime that the user goes to sleep, an average sleep midpoint time, an average sleep duration, or a combination thereof.

Some examples of the method, apparatuses, and non-transitory computer-readable medium described herein may further include operations, features, means, or instructions for overlaying the graphical representation of the averaging of the sleep pattern data of the first set of physiological data over the period of time against a representation of a twenty-four hour timespan.

Some examples of the method, apparatuses, and non-transitory computer-readable medium described herein may further include operations, features, means, or instructions for causing the graphical user interface of the user device to display a segment of the representation of the twenty-four hour timespan that comprises the averaging of the sleep pattern data of the first set of physiological data over the period of time.

In some examples of the method, apparatuses, and non-transitory computer-readable medium described herein, the segment represents the averaging of the sleep pattern data of the first set of physiological data over the period of time as a shaped portion having a first side indicating an average time the user goes to sleep, a second side indicating an average time the user wakes up, and a midpoint that may be positioned between the first side and the second side and indicates an average time of a sleep midpoint of the user.

Some examples of the method, apparatuses, and non-transitory computer-readable medium described herein may further include operations, features, means, or instructions for identifying a time of night associated with a nighttime temperature minimum based at least in part on receiving the first set of physiological data, wherein classifying the first set of physiological data into the circadian rhythm chronotype may be based at least in part on identifying the time of night associated with the nighttime temperature minimum.

Some examples of the method, apparatuses, and non-transitory computer-readable medium described herein may further include operations, features, means, or instructions for processing, by the application, the sleep pattern data of the first set of physiological data to extract at least a standard deviation of a sleep midpoint, a median wake time wake that the user wakes up, a median bedtime that the user goes to sleep, or a combination thereof, processing, by the application, the activity data of the first set of physiological data to extract at least an average metabolic equivalent of task (MET) value, a time that the user may be active, or both, processing, by the application, the nighttime temperature data to extract at least an average skin temperature, an average skin temperature for a plurality of highest temperature values of a consecutive twenty-four hour timespan, an average skin temperature for a plurality of lowest temperature values of a consecutive twenty-four hour timespan, or a combination thereof, and wherein classifying the first set of physiological data into the circadian rhythm chronotype may be based at least in part processing, by the application, the sleep pattern data, the activity data, and the nighttime temperature data.

Some examples of the method, apparatuses, and non-transitory computer-readable medium described herein may further include operations, features, means, or instructions for determining a misalignment between the received second set of physiological data and the determined circadian rhythm chronotype based at least in part on comparing the determined circadian rhythm chronotype and the received second set of physiological data.

In some examples of the method, apparatuses, and non-transitory computer-readable medium described herein, the message comprises a recommended time of day that the user may be active, a recommended wake time that the user wakes up, a recommended bedtime that the user goes to sleep, a recommended sleep duration, a recommended time of day that the user rests, a recommended time of day that the user may be focused, a sleep alignment message, a sleep misalignment message, or a combination thereof.

In some examples of the method, apparatuses, and non-transitory computer-readable medium described herein, the nighttime temperature data comprises continuous nighttime temperature data.

In some examples of the method, apparatuses, and non-transitory computer-readable medium described herein, the wearable device comprises a wearable ring device.

In some examples of the method, apparatuses, and non-transitory computer-readable medium described herein, the wearable device collects the first set of physiological data and the second set of physiological data from the user based on arterial blood flow, capillary blood flow, arteriole blood flow, or a combination thereof.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for determining a circadian rhythm chronotype on an application running on an operating system of a user device and associated with a wearable device, comprising:

receiving, from the wearable device, a first set of physiological data measured from a user by the wearable device collected over a period of time, the first set of physiological data comprising at least nighttime temperature data, activity data, and sleep pattern data;

receiving, from the wearable device, a second set of physiological data measured from the user by the wearable device collected over a previous sleep day, the second set of physiological data comprising at least additional sleep pattern data from the previous sleep day;

classifying, using a machine learning model, the first set of physiological data into the circadian rhythm chronotype based at least in part on inputting the first set of physiological data and a circadian rhythm adjustment model into the machine learning model, wherein classifying the first set of physiological data comprises adjusting one or more weights of one or more portions of the first set of physiological data based on the circadian rhythm adjustment model;

comparing, by the application that is configured for processing data received from the wearable device, the circadian rhythm chronotype and the second set of physiological data; and transmitting, to a graphical user interface of the user device, signaling causing the graphical user interface of the user device to display a message associated with the comparison, the circadian rhythm chronotype, the second set of physiological data, or a combination thereof.

2. The method of claim 1, further comprising:

causing the graphical user interface of the user device to display a graphical representation of an averaging of the sleep pattern data of the first set of physiological data over the period of time.

3. The method of claim 2, wherein the averaging of the sleep pattern data comprises an average wake time that the user wakes up, an average bedtime that the user goes to sleep, an average sleep midpoint time, an average sleep duration, or a combination thereof.

4. The method of claim 2, further comprising:

overlaying the graphical representation of the averaging of the sleep pattern data of the first set of physiological data over the period of time against a representation of a twenty-four hour timespan.

5. The method of claim 4, further comprising:

causing the graphical user interface of the user device to display a segment of the representation of the twenty-four hour timespan that comprises the averaging of the sleep pattern data of the first set of physiological data over the period of time.

6. The method of claim 5, wherein the segment represents the averaging of the sleep pattern data of the first set of physiological data over the period of time as a shaped portion having a first side indicating an average time the user goes to sleep, a second side indicating an average time the user wakes up, and a midpoint that is positioned between the first side and the second side and indicates an average time of a sleep midpoint of the user.

7. The method of claim 1, further comprising:

identifying a time of night associated with a nighttime temperature minimum based at least in part on receiving the first set of physiological data, wherein classifying the first set of physiological data into the circadian rhythm chronotype is based at least in part on identifying the time of night associated with the nighttime temperature minimum.

8. The method of claim 1, further comprising:

processing, by the application, the sleep pattern data of the first set of physiological data to extract at least a standard deviation of a sleep midpoint, a median wake time wake that the user wakes up, a median bedtime that the user goes to sleep, or a combination thereof;

processing, by the application, the activity data of the first set of physiological data to extract at least an average metabolic equivalent of task (MET) value, a time that the user is active, or both; and processing, by the application, the nighttime temperature data to extract at least an average skin temperature, an average skin temperature for a plurality of highest temperature values of a consecutive twenty-four hour timespan, an average skin temperature for a plurality of lowest temperature values of a consecutive twenty-four hour timespan, or a combination thereof, wherein classifying the first set of physiological data into the circadian rhythm chronotype is based at least in part on processing, by the application, the sleep pattern data, the activity data, and the nighttime temperature data.

9. The method of claim 1, further comprising:

determining a misalignment between the second set of physiological data and the circadian rhythm chronotype based at least in part on comparing the circadian rhythm chronotype and the second set of physiological data.

10. The method of claim 1, wherein the message comprises a recommended time of day that the user is active, a recommended wake time that the user wakes up, a recommended bedtime that the user goes to sleep, a recommended sleep duration, a recommended time of day that the user rests, a recommended time of day that the user is focused, a sleep alignment message, a sleep misalignment message, or a combination thereof.

11. The method of claim 1, wherein the nighttime temperature data comprises continuous nighttime temperature data.

12. The method of claim 1, wherein the wearable device comprises a wearable ring device.

13. The method of claim 1, wherein the wearable device collects the first set of physiological data and the second set of physiological data from the user based on arterial blood flow, capillary blood flow, arteriole blood flow, or a combination thereof.

14. An apparatus for determining a circadian rhythm chronotype on an application running on an operating system of user device and associated with a wearable device, comprising:

a processor;

memory coupled with the processor; and instructions stored in the memory and executable by the processor to cause the apparatus to:

receive, from the wearable device, a first set of physiological data measured from a user by the wearable device collected over a period of time, the first set of physiological data comprising at least nighttime temperature data, activity data, and sleep pattern data;

receive, from the wearable device, a second set of physiological data measured from the user by the wearable device collected over a previous sleep day, the second set of physiological data comprising at least additional sleep pattern data from the previous sleep day;

classify, using a machine learning model, the first set of physiological data into the circadian rhythm chronotype based at least in part on inputting the first set of physiological data and a circadian rhythm adjustment model into the machine learning model, wherein classifying the first set of physiological data comprises adjusting one or more weights of one or more portions of the first set of physiological data based on the circadian rhythm adjustment model;

compare, by the application that is configured for processing data received from the wearable device, the circadian rhythm chronotype and the second set of physiological data; and transmit, to a graphical user interface of the user device, signaling to cause the graphical user interface of the user device to display a message associated with the comparison, the circadian rhythm chronotype, the second set of physiological data, or a combination thereof.

15. The apparatus of claim 14, wherein the instructions are further executable by the processor to cause the apparatus to:

cause the graphical user interface of the user device to display a graphical representation of an averaging of the sleep pattern data of the first set of physiological data over the period of time.

16. The apparatus of claim 15, wherein the averaging of the sleep pattern data comprises an average wake time that the user wakes up, an average bedtime that the user goes to sleep, an average sleep midpoint time, an average sleep duration, or a combination thereof.

17. The apparatus of claim 15, wherein the instructions are further executable by the processor to cause the apparatus to:

overlay the graphical representation of the averaging of the sleep pattern data of the first set of physiological data over the period of time against a representation of a twenty-four hour timespan.

18. A non-transitory computer-readable medium storing code for determining a circadian rhythm chronotype on an application running on an operating system of user device and associated with a wearable device, the code comprising instructions executable by a processor to:

receive, from the wearable device, a first set of physiological data measured from a user by the wearable device collected over a period of time, the first set of physiological data comprising at least nighttime temperature data, activity data, and sleep pattern data;

receive, from the wearable device, a second set of physiological data measured from the user by the wearable device collected over a previous sleep day, the second set of physiological data comprising at least additional sleep pattern data from the previous sleep day;

classify, using a machine learning model, the first set of physiological data into the circadian rhythm chronotype based at least in part on inputting the first set of physiological data and a circadian rhythm adjustment model into the machine learning model, wherein classifying the first set of physiological data comprises adjusting one or more weights of one or more portions of the first set of physiological data based on the circadian rhythm adjustment model;

compare, by the application that is configured for processing data received from the wearable device, the circadian rhythm chronotype and the second set of physiological data; and transmit, to a graphical user interface of the user device, signaling to cause the graphical user interface of the user device to display a message associated with the comparison, the circadian rhythm chronotype, the second set of physiological data, or a combination thereof.

19. The non-transitory computer-readable medium of claim 18, wherein the instructions are further executable by the processor to:

cause the graphical user interface of the user device to display a graphical representation of an averaging of the sleep pattern data of the first set of physiological data over the period of time.

20. The non-transitory computer-readable medium of claim 19, wherein the averaging of the sleep pattern data comprises an average wake time that the user wakes up, an average bedtime that the user goes to sleep, an average sleep midpoint time, an average sleep duration, or a combination thereof.

* * * * *